(12) United States Patent
Kimura et al.

(10) Patent No.: US 8,386,020 B2
(45) Date of Patent: Feb. 26, 2013

(54) MEDICAL-DEVICE GUIDANCE SYSTEM

(75) Inventors: Atsushi Kimura, Tokyo (JP); Akio Uchiyama, Kanagawa (JP); Ryoji Sato, Tokyo (JP); Atsushi Chiba, Tokyo (JP)

(73) Assignee: Olympus Corporation, Tokyo (JP)

( * ) Notice: Subject to any disclaimer, the term of this patent is extended or adjusted under 35 U.S.C. 154(b) by 805 days.

(21) Appl. No.: 12/307,490

(22) PCT Filed: Jun. 29, 2007

(86) PCT No.: PCT/JP2007/063080
§ 371 (c)(1),
(2), (4) Date: Jun. 29, 2009

(87) PCT Pub. No.: WO2008/004497
PCT Pub. Date: Jan. 10, 2008

(65) Prior Publication Data
US 2010/0022835 A1   Jan. 28, 2010

(30) Foreign Application Priority Data
Jul. 5, 2006   (JP) .................... 2006-185308

(51) Int. Cl.
*A61B 5/055*   (2006.01)
*A61B 1/00*   (2006.01)
(52) U.S. Cl. .......... 600/424; 600/114; 600/118
(58) Field of Classification Search ............ 600/11, 600/109, 114, 118, 420, 424; 702/183
See application file for complete search history.

(56) References Cited

U.S. PATENT DOCUMENTS

| 2002/0169361 | A1 | 11/2002 | Taniguchi et al. |
| 2004/0236180 | A1 | 11/2004 | Uchiyama et al. |
| 2005/0216231 | A1* | 9/2005 | Aoki et al. ............ 702/183 |
| 2006/0041181 | A1 | 2/2006 | Viswanathan et al. |
| 2007/0260139 | A1* | 11/2007 | Minai et al. ............ 600/420 |

FOREIGN PATENT DOCUMENTS

| JP | 2002-325721 | 11/2002 |
| JP | 2004-298560 | 10/2004 |
| JP | 2006-263167 | 10/2006 |
| JP | 2007-216040 | 8/2007 |
| WO | WO 2006/025400 A1 | 3/2006 |

OTHER PUBLICATIONS

Extended Supplementary European Search Report dated Feb. 3, 2010.

* cited by examiner

*Primary Examiner* — Michael Rozanski
(74) *Attorney, Agent, or Firm* — Scully Scott Murphy & Presser, PC

(57) ABSTRACT

A situation where a medical device is outside a region suitable for guidance control thereof can be easily coped with. Included are a medical device provided with a magnet; a guiding unit (5X-1, 5X-2, 5Y-1, 5Y-2, 5Z-1, 5Z-2) that forms a control magnetic field for guidance control of the medical device, inside a prescribed control area; a detection unit (7Y-1, 7Y-2) that detects positional information of the medical device; and a computational unit that judges that the medical device has gone outside the control area on the basis of an output from the detection unit (7Y-1, 7Y-2) and calculates a direction for returning the medical device to the control area, wherein a signal-waveform calculating unit (21) stops forming the control magnetic field when the medical device is outside the control area.

18 Claims, 15 Drawing Sheets

MEDICAL-DEVICE GUIDANCE SYSTEM

TECHNICAL FIELD

The present invention relates to a medical-device guidance system.

BACKGROUND ART

Recently, there has been research and development to realize medical devices, as typified by swallowable capsule endoscopes etc., that can be introduced into a subject, e.g. a person to be examined, by swallowing so as to pass through a gastrointestinal tract and acquire images at a target position inside the gastrointestinal tract.

In order to guide such medical devices to a specific location in the gastrointestinal tract, currently, means for detecting at which position the medical device is located in the gastrointestinal tract and for performing guidance control of the medical device are required. Known means for guidance control of the medical device involves controlling the position etc. of an endoscope by installing a magnet inside the endoscope and using an external magnetic field (for example, see Patent Document 1).

On the other hand, one known method of detecting the position etc. of the medical device is a magnetic position detection method. One known magnetic position detection method is a technique in which a source coil for generating a magnetic field is provided in the medical device, and the position etc. of the medical device is specified by detecting the magnetic field generating from the source coil with a magnetic-field detection unit etc. (for example, see Patent Document 2).

Patent Document 1: Japanese Unexamined Patent Application, Publication No. 2004-298560

Patent Document 2: Japanese Unexamined Patent Application, Publication No. 2002-325721

DISCLOSURE OF INVENTION

In medical-device guidance systems provided with guidance apparatuses for guidance control of medical devices via magnetic fields, generally the region suitable for guidance control of the medical device (hereinafter referred to as control region) can be enlarged by making the generated magnetic field uniform by using a Helmholtz arrangement for the coil arrangement. However, around the control region, there is an area where the guidance controllability of the medical device is reduced, or where the maneuverability of the medical device is decreased, which thus restricts the control region.

For example, even in cases where the coils are in a Helmholtz arrangement, because the size of each coil is restricted, the control region is restricted. One problem is that, in outer areas of the control region, for example, in areas close to the coils, because the uniformity of the magnetic field is low, or the magnetic field direction is shifted from the intended direction, there is a risk that the guidance maneuverability of the medical device will be decreased.

One known method of solving the problem described above is a method in which a movable portion is provided in the magnetic guidance apparatus, and the guidance apparatus is made to move so as to track the motion of the medical device.

However, if the control region of the guidance device covers, to a certain extent, an inspection area where inspection is performed by the medical device, when performing the tracking motion described above, the movable portion of the guidance apparatus is always moving, thus necessitating a safety mechanism. One problem, as a result, is that the guidance apparatus becomes complicated.

The present invention has been conceived in order to solve the problems described above, and an object thereof is to provide a medical-device guidance system that can prevent the medical device from deviating a great distance from a region suitable for guidance control thereof.

In order to realize the object described above, the present invention provides the following solutions.

A first aspect of the present invention provides a medical-device guidance system including a medical device with a magnet; a guiding unit that forms a control magnetic field for guidance control of the medical device, inside a prescribed control area; a detection unit that detects positional information of the medical device; a computational unit that judges that the medical device has gone outside the control area on the basis of an output from the detection unit and that calculates a direction for returning the medical device to the control area; and a control unit that controls the guiding unit on the basis of an output from the computational unit, wherein the control unit stops formation of the control magnetic field when the medical device goes outside the control area.

According to the first aspect of the present invention, because the guiding unit, the detection unit, the computational unit, and the control unit are provided, it is possible to prevent the medical device from deviating a great distance from the control area suitable for guidance control of the medical device.

Because the guiding unit forms the control magnetic field for guidance control of the medical device inside the control area, it is possible to guide the medical device, located inside the control area, in a prescribed direction. The detection unit can detect the positional information of the medical device. The computational unit receives a signal from the detection unit and judges in which direction the medical device goes beyond the control region. At the same time, the computational unit can output a signal indicating that the medical device has gone outside the control area. The control unit can control the guiding unit on the basis of the signal from the computational unit. Because the guiding unit can stop forming the control magnetic field on the basis of the output from the control unit, it is possible to easily prevent the medical device from deviating a great distance from the control area. In other words, because formation of the control magnetic field is stopped, the force acting on the medical device due to the control magnetic field vanishes, and it is possible to relatively move the medical device and the control area to easily move the medical device inside the control area. Furthermore, because guidance control of the medical device by the control magnetic field is also stopped, it is possible to prevent the medical device from going farther from the control area due to an erroneous operation.

In the above-described invention, preferably, the medical device is introduced into a body cavity of a subject, and a driver is provided that moves the subject on the basis of an output from the control unit.

By doing so, because the driver is provided, it is possible to prevent the medical device from deviating a great distance from the control area suitable for guidance control of the medical device.

By moving the subject in which the medical device is introduced using the driver, it is possible to return the medical device inside the control area. Because the driver automatically moves the subject on the basis of the output from the control unit, it is possible to easily prevent the medical device from deviating a great distance from the control area, compared with a method in which the operator moves the medical device to return the medical device inside the control area.

In the above-described invention, preferably, on the basis of the output from the computational unit, the control unit forms the control magnetic field for moving the medical device by a prescribed amount in the direction for returning the medical device to the control area and thereafter stops forming the control magnetic field.

By doing so, by controlling the control magnetic field, the control unit can move the medical device by a prescribed amount in a direction for returning it to the control area. Because the medical device approaches the control area by a prescribed amount, guidance control of the medical device becomes easier in subsequent handling, and it is possible to easily prevent the medical device from deviating a great distance from the control area. At the same time, because the moving distance is restricted to a prescribed amount, the medical device does not move to a position away from a position outside the control area. Therefore, the operator of the medical device can easily find the position of the medical device, and it is possible to easily prevent the medical device from deviating a great distance from the control area.

Because the control unit forms the control magnetic field on the basis of the output from the computational unit, it is possible to automatically return the medical device inside the control area.

After moving the medical device in a direction for returning it to the control area, the control unit stops forming the control magnetic field; therefore, it is possible to easily prevent the medical device from deviating a great distance from the control area.

In the above-described invention, preferably, the medical device includes a detected portion to be detected by the detection unit, and the detection unit is disposed in the vicinity of a boundary region of the control area.

By doing so, because the detected portion and the detection unit are provided, it is possible to calculate the positional information of the medical device.

Because the detected portion is provided in the medical device, it is possible to detect the position of the detected portion. Because the detection unit is disposed in the vicinity of the boundary region of the control area, it is possible to easily detect that the detected portion, in other words, the medical device, has gone outside the control area.

Here, possible examples of the detection unit are a metal sensor, an ultrasonic sensor, etc. When using a metal sensor as the detection unit, a metal member may be used as the detected portion. When using an ultrasonic sensor as the detection unit, a reflecting member that reflects ultrasonic waves may be used as the detected portion.

In the above-described invention, preferably, the medical device includes a magnetic induction coil; and the detection unit includes a position-detection-magnetic-field forming unit that forms a position-detection magnetic field for inducing an induced magnetic field in the magnetic induction coil, a magnetic-field detection unit that detects the induced magnetic field generated by the magnetic induction coil, and a position calculating unit that calculates positional information of the medical device on the basis of an output from the magnetic-field detection unit.

By doing so, because the medical device includes the magnetic induction coil and because the detection unit includes the position-detection-magnetic-field forming unit, the magnetic-field detection unit, and the position calculating unit, the detection unit can calculate the positional information of the medical device.

Because the medical device includes the magnetic induction coil, by applying a position-detection magnetic field, it is possible to generate an induced magnetic field from the medical device (magnetic induction coil). Because the detection unit includes the position-detection-magnetic-field forming unit, it is possible to form the position-detection magnetic field in the control area and to generate an induced magnetic field from the medical device located inside the control area. Because the detection unit includes the magnetic-field detection unit for detecting the induced magnetic field generated by the medical device, it is possible to obtain from the magnetic-field detection unit an output signal according to the strength of the induced magnetic field. The position calculating unit can calculate at which position the medical device is located relative to the magnetic-field detection unit on the basis of the output signal from the magnetic-field detection unit. The position calculating unit can output the above-mentioned calculation result to the computational unit.

In the above-described invention, preferably, the medical device includes a magnetic-field generator that generates a magnetic field; and the detection unit includes a magnetic-field detection unit that detects the magnetic field generated by the magnetic-field generator, and a position calculating unit that calculates positional information of the medical device on the basis of an output from the magnetic-field detection unit.

By doing so, because the medical device includes the magnetic-field generator and because the detection unit includes the magnetic-field detection unit and the position calculating unit, the detection unit can detect that the medical device has gone outside the control area.

The magnetic field generator, provided in the medical device, generates its own magnetic field towards the outside. Because the detection unit includes the magnetic-field detection unit for detecting the magnetic field generated by the magnetic-field generator, the detection unit can obtain from the magnetic-field detection unit an output signal according to the strength of the received magnetic field. The position calculating unit can calculate at which position the medical device is located relative to the magnetic-field detection unit on the basis of the output signal from the magnetic-field detection unit. The position calculating unit can output the above-mentioned calculation result to the computational unit.

In the above-described invention, preferably the medical device includes a wireless transmission unit that transmits radio waves; and the detection unit includes a plurality of wireless reception units that receive the radio waves, and a position calculating unit that calculates positional information of the medical device on the basis of output signals from the plurality of wireless reception units.

By doing so, because the medical device includes the wireless transmission unit and because the detection unit includes the wireless reception unit and the position calculating unit, the detection unit can detect that the medical device has gone outside the control area.

The medical device includes the wireless transmission unit, and radio waves are transmitted towards the outside from the wireless transmission unit. Because the detection unit includes the plurality of wireless reception units that receive the radio waves transmitted from the wireless transmission unit, the detection unit can obtain from the plurality of wireless reception units a plurality of output signals according to the strengths of the received radio waves. The position calculating unit can calculate at which position the medical device is located relative to the plurality of wireless reception units on the basis of the output signals from the wireless reception units. The position calculating unit can output the above-mentioned calculation result to the computational unit.

A second aspect of the present invention provides a medical-device guidance system control method for guidance control, by a control magnetic field formed in a control area, of a medical device in which a magnetic field can be induced and which is disposed inside the control area, the medical-device guidance system control method including a detecting step of detecting positional information of the medical device; a calculating step of judging that the medical device has gone outside the control area and calculating a direction for returning the medical device to the control area; an instructing step of outputting an instruction for moving the medical device in a direction for returning the medical device to the control area; and a stopping step of stopping formation of the control magnetic field.

According to the second aspect of the present invention, because the detecting step, the calculating step, the instructing step, and the stopping step are provided, it is possible to easily prevent the medical device from deviating a great distance from the control area suitable for guidance control of the medical device.

By providing the detecting step, it is possible to detect the positional information of the medical device. By providing the calculating step, it is possible to judge that the medical device has gone outside the control area suitable for guidance control, and it is possible to prevent an inability to perform guidance control of the medical device. By providing the calculating step, it is possible to calculate the direction for returning the medical device to the control area, and it is possible to easily prevent the medical device from deviating a great distance from the control area. By providing the instructing step, for example, the operator of the medical-device guidance system can easily find the direction for returning the medical device to the control area, and it is possible to easily prevent the medical device from deviating a great distance from the control area. By providing the stopping step, formation of the control magnetic field can be stopped, and it is possible to easily prevent the medical device from deviating a great distance from the control area. In other words, the force acting on the medical device due to the control magnetic field vanishes, and it is possible to relatively move the medical device and the control area to easily move the medical device inside the control area. Furthermore, because guidance control of the medical device by the control magnetic field is also stopped, it is possible to prevent the medical device from going farther away from the control area due to an erroneous operation.

The above-described invention preferably includes, between the instructing step and the stopping step, a moving step of relatively moving the medical device and the control area by a prescribed amount in a direction for returning the medical device to the control area.

By doing so, because the moving step is provided, it is possible to easily prevent the medical device from deviating a great distance from the control area suitable for guidance control of the medical device.

Because the moving step is provided, the medical device approaches by a prescribed amount in a direction for returning to the control area. Therefore, guidance control of the medical device becomes easier in subsequent handling, and it is possible to easily prevent the medical device from deviating a great distance from the control area. At the same time, because the moving distance is restricted to a prescribed amount, the medical device does not move to a position away from a position outside the control area. Therefore, the operator of the medical device can easily find the position of the medical device, and it is possible to easily prevent the medical device from deviating a great distance from the control area.

With the medical-device guidance system of the present invention, because it includes the guiding unit that forms the control magnetic field for guidance control of the medical device inside the control area; the detection unit that detects the positional information of the medical device; the computational unit that judges that the medical device has gone outside the control area on the basis of the output from the detection unit and calculates the direction for returning the medical device to the control area; and the control unit for stopping formation of the control magnetic field, an advantage is afforded in that it is possible to easily prevent the medical device from deviating a great distance from the control area suitable for guidance control thereof.

Figure 1:
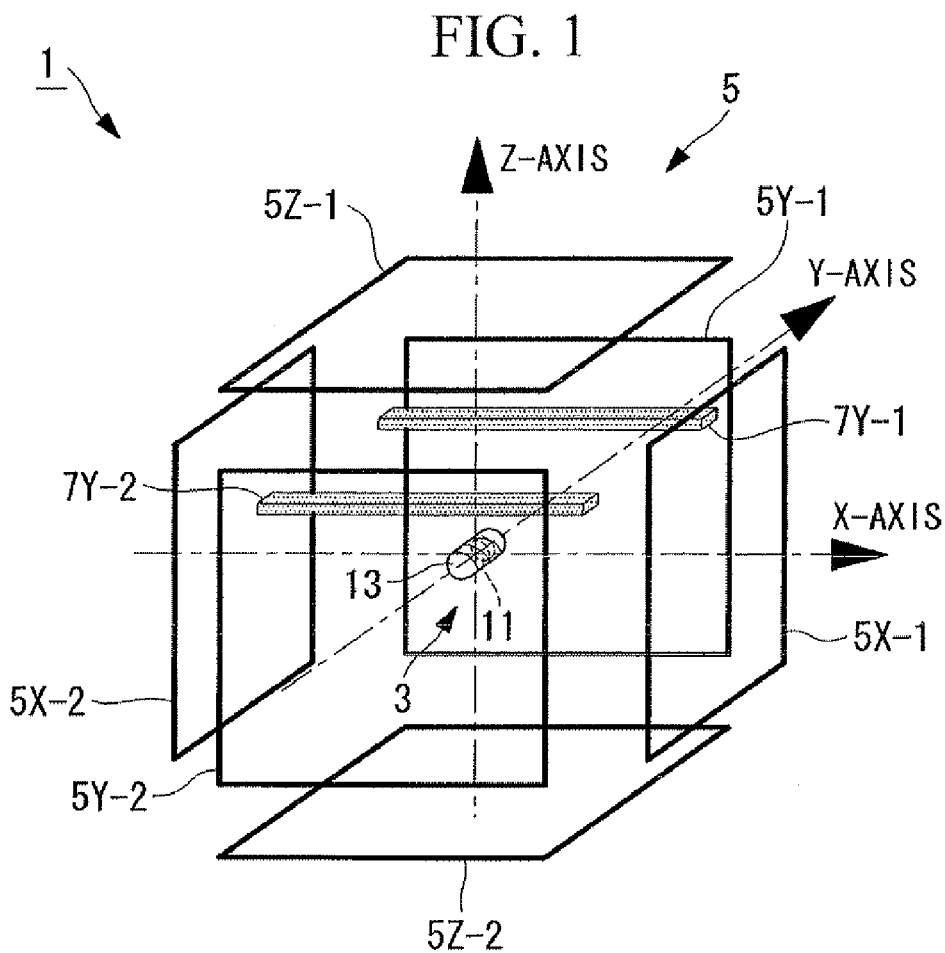
FIG. 1 is a schematic diagram for explaining the outer configuration of a capsule-medical-device guidance system of a first embodiment of the present invention.

EXPLANATION OF REFERENCE SIGNS 1, 101, 201, 301, 401: capsule-medical-device guidance system (medical-device guidance system)
3, 103, 203, 303: capsule medical device (medical device)
5: coil unit (guiding unit)
5X-1, 5X-2, 5Y-1, 5Y-2, 5Z-1, 5Z-2: guidance-magnetic-field generating coil (guiding unit)
7Y-1, 7Y-2: metal sensor (detection unit)
9: subject
11: permanent magnet (magnet)
15, 115: metal portion (detected portion)
17: control area
21, 121, 421: control unit
25: display unit
27X, 27Y, 27Z: signal generator (guiding unit)
29X, 29Y, 29Z: guidance-magnetic-field generating coil driver (guiding unit)
31: driver
133, 233, 333: position calculating unit (detection unit)
35: computational unit (computational unit)
105: position-detection magnetic-field generating coil (position-detection magnetic-field forming unit)
107: magnetic-field detection unit (detection unit)
307: wireless reception unit (detection unit)
315: wireless transmission unit
308: antenna (wireless reception unit, detection unit)

BEST MODE FOR CARRYING OUT THE INVENTION

First Embodiment

A capsule-medical-device guidance system according to a first embodiment of the present invention will be described below with reference to FIGS. 1 to 10.

FIG. 1 is a schematic view for explaining the external configuration of the capsule-medical-device guidance system of this embodiment.

As shown in FIG. 1, a capsule-medical-device guidance system (medical-device guidance system) 1 includes a capsule medical device (medical device) 3 which is introduced into a subject etc., a coil unit (guiding unit) 5 which forms a guidance magnetic field (control magnetic field), and metal sensors (detection units) 7Y-1 and 7Y-2.

The capsule medical device 3 is guided inside a tract in the body cavity of a subject 9 in order to perform a medical procedure, such as observation, diagnosis, or treatment, of an inner surface of the gastrointestinal tract. As shown in FIG. 1, the capsule medical device 3 is provided with a permanent magnet (magnet) 11, a helical section 13, and a metal portion (detected portion). The permanent magnet 11 is provided in the interior of the capsule medical device 3 and is secured to the capsule medical device 3 so that motion of the permanent magnet 11 is transferred to the capsule medical device 3. The helical section 13 converts rotary motion of the capsule medical device 3 to a propulsive force. The helical section 13 is a spiral projecting portion provided on the outer surface of the capsule medical device 3. The helical section 13 is provided such that the center axis is identical to or substantially parallel to the rotation axis of the capsule medical device 3. The metal portion is the part detected by the metal sensors 7Y-1 and 7Y-2.

As described above, the capsule medical device 3 may be provided with an independent metal portion to be detected by the metal sensors 7Y-1 and 7Y-2. It is not particularly limited, however; in the case where another device, for example, the above-described device for performing a medical procedure, built into the capsule medical device 3 is detected by the metal sensors 7Y-1 and 7Y-2, a metal portion need not be independently provided.

The coil unit 5 performs guidance control of the capsule medical device 3 by forming a guidance magnetic field inside a control area. As shown in FIG. 1, the coil unit 5 includes a pair of guidance-magnetic-field generating coils (guiding units) 5X-1 and 5X-2 disposed substantially perpendicular to the X-axis; a pair of guidance-magnetic-field generating coils (guiding units) 5Y-1 and 5Y-2 disposed substantially perpendicular to the Y-axis; and a pair of guidance-magnetic-field generating coils (guiding units) 5Z-1 and 5Z-2 disposed substantially perpendicular to the Z-axis. The pair of guidance-magnetic-field generating coils 5X-1 and 5X-2, the pair of guidance-magnetic-field generating coils 5Y-1 and 5Y-2, and the pair of guidance-magnetic-field generating coils 5Z-1 and 5Z-2 are disposed such that the coil pairs face each other in a Helmholtz arrangement. The guidance-magnetic-field generating coils 5X-1, 5X-2, 5Y-1, 5Y-2, 5Z-1, and 5Z-2 are disposed in the form of a cube or cuboid so as to form a control area 17 in the interior.

As described above, the pair of guidance-magnetic-field generating coils 5X-1 and 5X-2, the pair of guidance-magnetic-field generating coils 5Y-1 and 5Y-2, and the pair of guidance-magnetic-field generating coils 5Z-1 and 5Z-2 are disposed such that normals of each coil form three orthogonal axes. They are not particularly limited, however; they need not form three orthogonal axes.

As described above, the pair of guidance-magnetic-field generating coils 5X-1 and 5X-2; the pair of guidance-magnetic-field generating coils 5Y-1 and 5Y-2; and the pair of guidance-magnetic-field generating coils 5Z-1 and 5Z-2 may be disposed such that the pairs of coils face each other in a Helmholtz arrangement. They are not particularly limited, however; they need not be disposed opposite each other in a Helmholtz arrangement.

Figure 2:
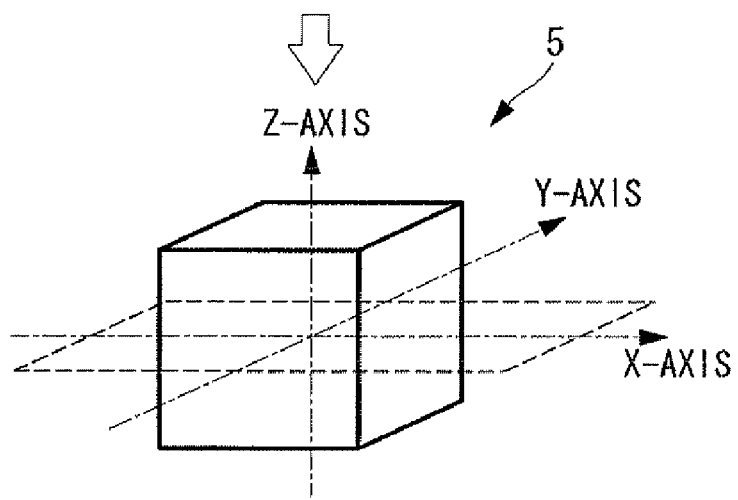
FIG. 2 is a diagram for explaining the position of a plane used in explaining a control area in the capsule-medical-device guidance system in FIG. 1.
Figure 3:
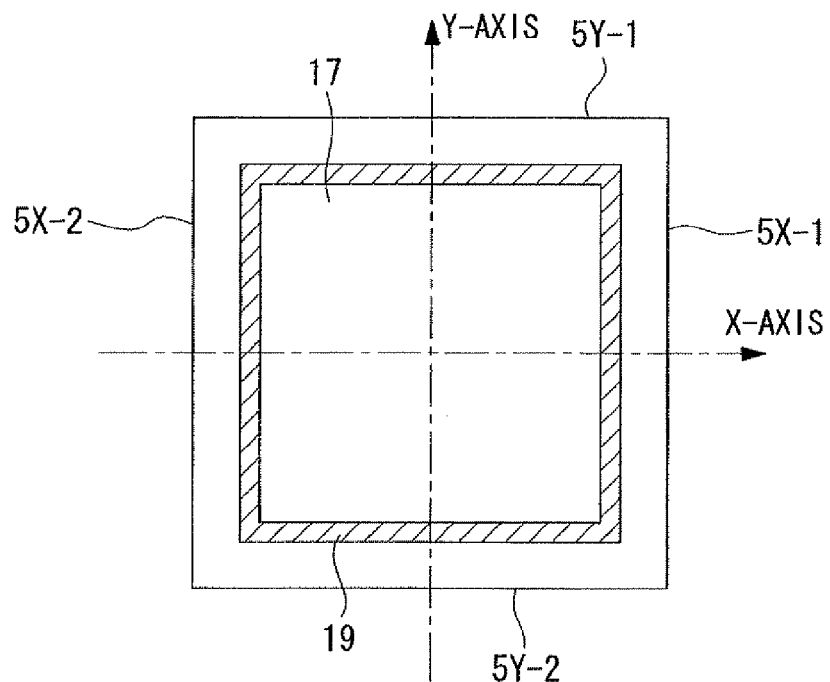
FIG. 3 is a schematic diagram showing a control area in the plane explained using FIG. 2.
Figure 4:
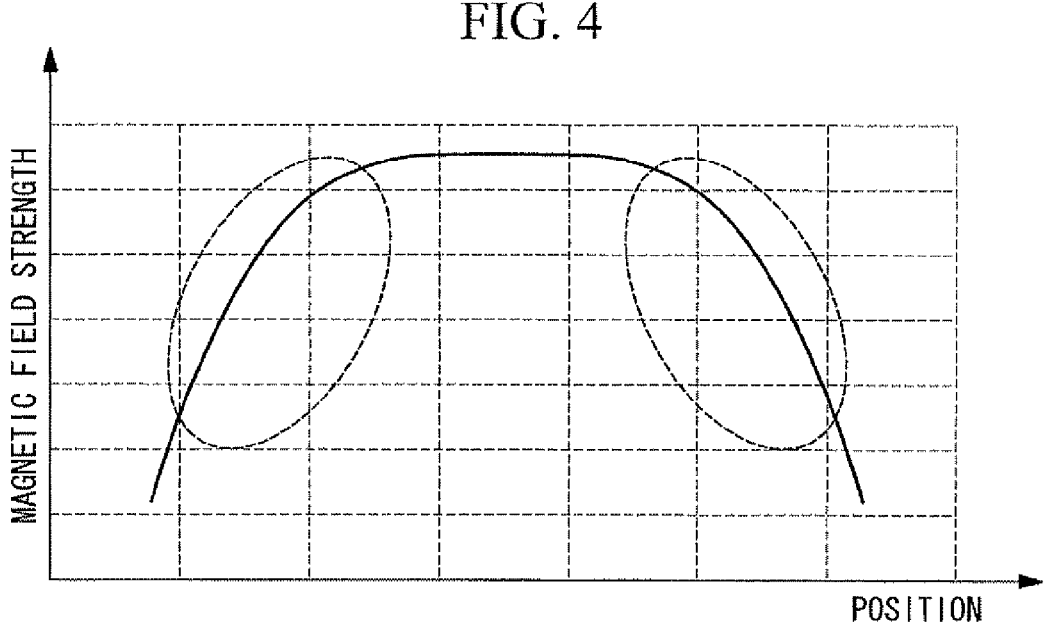
FIG. 4 is a diagram for explaining a magnetic field intensity distribution in the control area in FIG. 3, and in an area in the vicinity thereof.

FIG. 2 is a diagram for explaining the position of a plane used in explaining the control area in the capsule-medical-device guidance system in FIG. 1. FIG. 3 is a schematic diagram showing the control area in the plane explained with FIG. 2. FIG. 4 is a diagram for explaining a magnetic field intensity distribution in the control area in FIG. 3, and in an area in the vicinity thereof.

The control area and the adjacent area, which are set inside a region surrounded by the guidance-magnetic-field generating coils 5X-1, 5X-2, 5Y-1, 5Y-2, 5Z-1, and 5Z-2, will now be described.

As shown in FIG. 2, the coil unit 5 will be described when applied to a case where a plane cut along the X-Y plane is viewed from the positive direction on the Z-axis. In this case, as shown in FIG. 3, the control area 17 is defined at the center side of the region surrounded by the guidance-magnetic-field generating coils 5X-1, 5X-2, 5Y-1, and 5Y-2, and an adjacent area 19, where the controllability is reduced, is defined between the control area 17 and the guidance-magnetic-field generating coils 5X-1, 5X-2, 5Y-1, and 5Y-2.

A guidance magnetic field having a magnetic field intensity distribution like that shown in FIG. 4 is formed in the region surrounded by the guidance-magnetic-field generating coils 5X-1, 5X-2, 5Y-1, 5Y-2, 5Z-1, and 5Z-2. Regarding the pair of guidance-magnetic-field generating coils 5X-1 and 5X-2, the pair of guidance-magnetic-field generating coils 5Y-1 and 5Y-2, and the pair of guidance-magnetic-field generating coils 5Z-1 and 5Z-2, because the pairs of coils are disposed opposite each other in a Helmholtz arrangement, a region of substantially uniform magnetic field intensity (a region where the gradient of the magnetic field intensity is flat) is formed inside the above-described region. This region with substantially uniform magnetic field intensity in FIG. 4 is defined as the control area 17 in FIG. 3, and the region where the magnetic field gradient of the magnetic field in FIG. 4 is strong (the region enclosed by the ellipses) is defined as the adjacent area 19 in FIG. 3. Because the adjacent area 19 has a strong magnetic field gradient of the magnetic field intensity, the maneuverability of the capsule medical device 3 is somewhat reduced compared with the control area 17.

Figure 5:
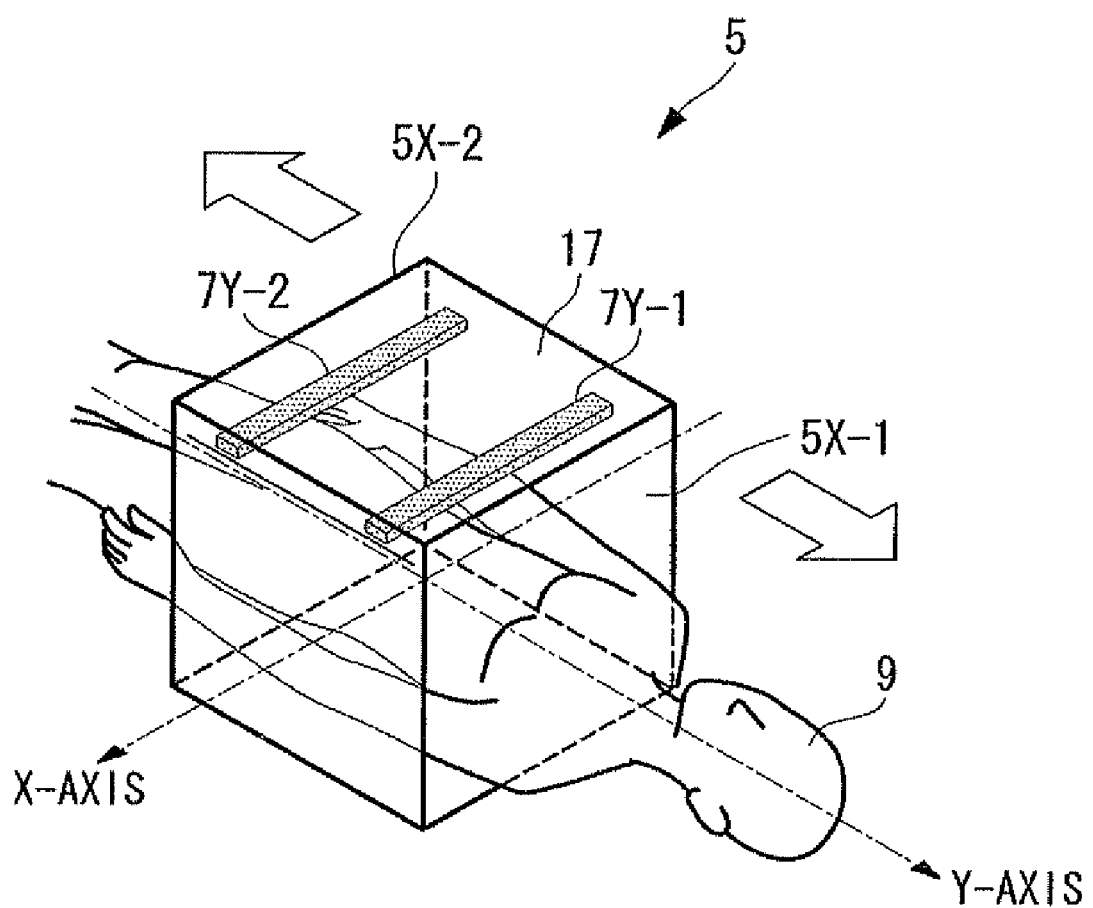
FIG. 5 is a schematic diagram showing the relative positional relationship between the capsule-medical-device guidance system in FIG. 1 and a subject.

FIG. 5 is a schematic diagram showing the relative positional relationship between the capsule-medical-device guidance system in FIG. 1 and a subject.

The metal sensors 7Y-1 and 7Y-2 detect positional information of the capsule medical device 3. As shown in FIG. 1, the metal sensor 7Y-1 is disposed in a region close to the guidance-magnetic-field generating coil 5Y-1, and the metal sensor 7Y-2 is disposed in a region close to the guidance-magnetic-field generating coil 5Y-2. The metal sensors 7Y-1 and 7Y-2 are disposed so as to extend along the X-axis, and they are disposed inside the adjacent area 19 (see FIG. 3).

In this embodiment, as shown in FIG. 5, in order to give an explanation when applied to a case where the subject 9 moves in the axial direction of the Y-axis, the metal sensors 7Y-1 and 7Y-2, which are in the regions close to the respective guidance-magnetic-field generating coils 5X-1 and 5X-2, are disposed so as to extend along the X-axis. Because the capsule medical device 3 moves together with the motion of the subject 9, the capsule medical device 3 has a high possibility of going outside the control area 17 in a direction along the Y-axis. In the direction along the X-axis and the direction along the Z-axis, the possibility of going outside the control area 17 is low, and therefore, metal sensors extending along the Y-axis and the Z-axis are not provided. Thus, the positions at which the metal sensors 7Y-1 and 7Y-2 are disposed, and the number that are disposed, are not particularly limited; they can be arbitrarily changed according to the moving direction etc. of the subject 9.

Figure 6:
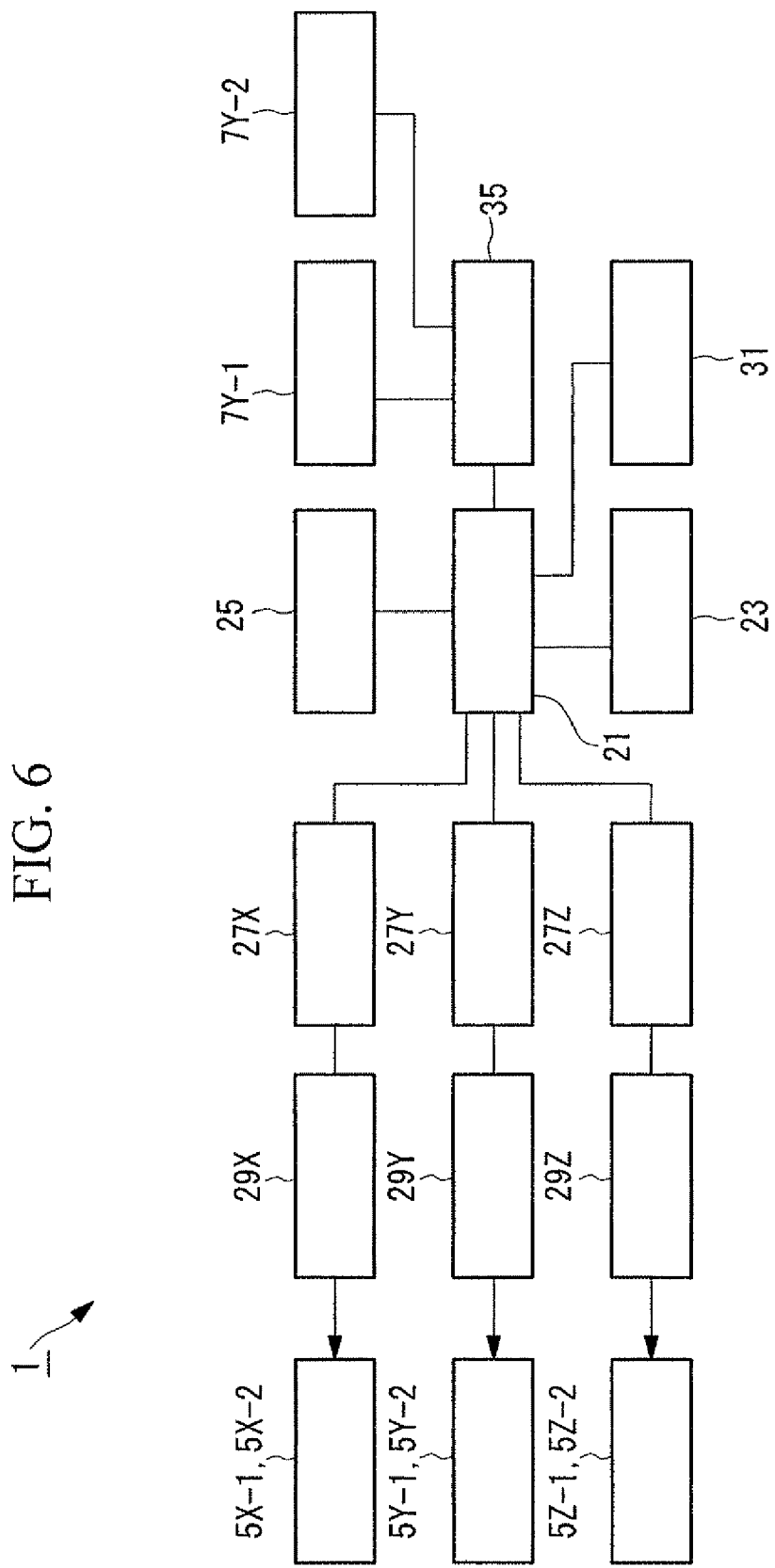
FIG. 6 is a block diagram for explaining a circuit configuration in the capsule-medical-device guidance system in FIG. 1.

FIG. 6 is a block diagram for explaining the circuit configuration in the capsule-medical-device guidance system in FIG. 1.

As shown in FIG. 6, the capsule-medical-device guidance system 1 further includes a control unit 21; an operating unit 23; a display unit 25; signal generators (guiding units) 27X, 27Y, and 27Z; guidance-magnetic-field generating coil drivers (guiding units) 29X, 29Y, and 29Z; a driver 31, and a computational unit 35.

The computational unit 35 determines that the capsule medical device 3 has gone outside the control area 17 on the basis of detection signals input from the metal sensors 7Y-1 and 7Y-2. The computational unit 35 can determine whether the direction in which the capsule medical device 3 goes outside the control area 17 is either the positive direction or the negative direction on the Y-axis by determining from which of the metal sensors 7Y-1 and 7Y2 a detection signal is output. Additionally, the computational unit 35 calculates a direction for returning the capsule medical device 3 to the control area 17.

Using the operating unit 23, an operator inputs instructions for the capsule-medical-device guidance system 1, such as the guidance direction of the capsule medical device 3. The operator instruction input to the operating unit 23 is input to the control unit 21.

The display unit 25 displays to the operator the direction for returning the capsule medical device 3 to the control area 17, which the computational unit 35 calculated.

The control unit 21 calculates a control signal for generating the guidance magnetic field on the basis of the input from the operating unit 23. Then, an instruction for generating the calculated waveform is output to the signal generators 27X, 27Y, and 27Z. The control unit 21 performs control for stopping the guidance magnetic field on the basis of the computed results from the computational unit 35. In addition, the control unit 21 inputs to the display unit 25 an instruction for displaying the required information to the operator.

The signal generators 27X, 27Y, and 27Z produce AC signals for generating a guidance magnetic field from the guidance-magnetic-field generating coil drivers 29X, 29Y, and 29Z. As shown in FIG. 6, control signals are input to the signal generators 27X, 27Y, and 27Z from the control unit 21, and the AC signals produced in the signal generators 27X, 27Y, and 27Z are input to the respective guidance-magnetic-field generating coil drivers 29X, 29Y, and 29Z.

Figure 7:
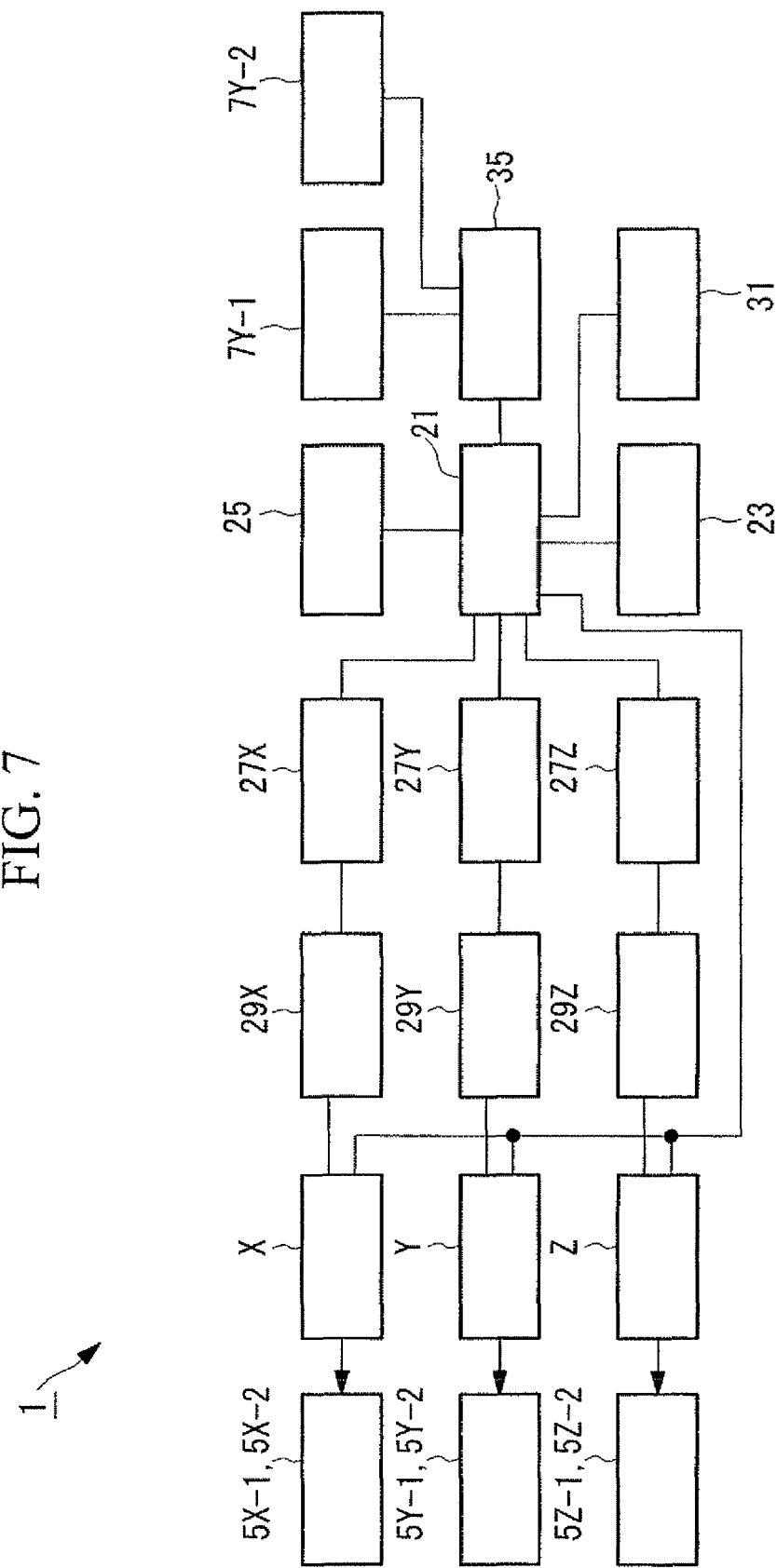
FIG. 7 is another block diagram for explaining the circuit configuration in the capsule-medical-device guidance system in FIG. 1.

FIG. 7 is another block diagram for explaining the circuit configuration in the capsule-medical-device guidance system in FIG. 1. The basic configuration in the block diagram in FIG. 7 is the same as the block diagram in FIG. 6 but differs in that the capsule-medical-device guidance system 1 is further provided with switching units X, Y, and Z.

The switching units X, Y, and Z control the electrical currents flowing into the guidance-magnetic-field generating coils 5X-1 and 5X-2, the guidance-magnetic-field generating coils 5Y-1 and 5Y-2, and the guidance-magnetic field generating coils 5Z-1 and 5Z-2 on the basis of the control signals input from the control unit 21, as described below.

Control signals are input from the control unit 21 to the switching units X, Y, and Z. The switching unit X constitutes a current circuit together with the guidance-magnetic-field generating coil driver 29X and the guidance-magnetic-field generating coils 5X-1 and 5X2; the switching unit Y constitutes a current circuit together with the guidance-magnetic-field generating coil driver 29Y and the guidance-magnetic-field generating coils 5Y-1 and 5Y-2; and the switching unit Z constitutes a current circuit together with the guidance-magnetic-field generating coil driver 29Z and the guidance-magnetic-field generating coils 5Z-1 and 5Z-2.

Figure 8:
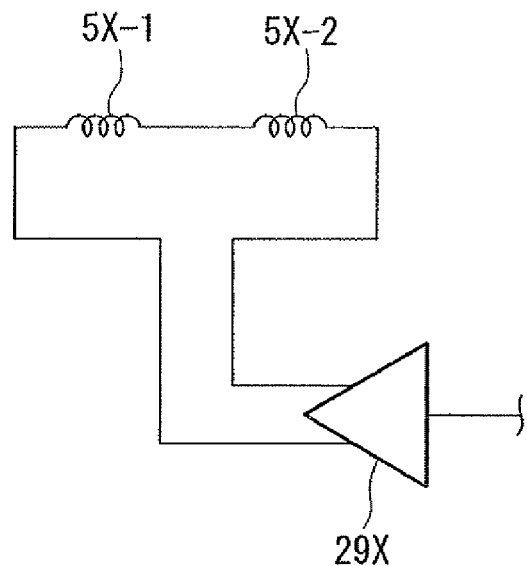
FIG. 8 is a circuit diagram showing the relationship between a guidance-magnetic-field generating coil and a guidance-magnetic-field generating coil driver in FIG. 6.

FIG. 8 is a circuit diagram showing the relationship between the guidance-magnetic-field generating coils and the guidance-magnetic-field generating coil drivers in FIG. 6.

The guidance-magnetic-field generating coil drivers 29X, 29Y, and 29Z amplify the AC signals input from the respective signal generators 27X, 27Y, and 27Z and output them to the guidance-magnetic-field generating coils 5X-1 and 5X-2, the guidance-magnetic-field generating coils 5Y-1 and 5Y-2, and the guidance-magnetic-field generating coils 5Z-1 and 5Z-2. As shown in FIG. 6, the AC signals produced in the respective signal generators 27X, 27Y, and 27Z are input to the guidance-magnetic-field generating coil drivers 29X, 29Y, and 29Z. The AC signals amplified in the guidance-magnetic-field generating coil drivers 29X, 29Y, and 29Z are output to the respective guidance-magnetic-field generating coils 5X-1 and 5X-2, the guidance-magnetic-field generating coils 5Y-1 and 5Y-2, and the guidance-magnetic-field generating coils 5Z-1 and 5Z-2.

As shown in FIG. 8, the guidance-magnetic-field generating coil driver 29X forms a single closed circuit with the guidance-magnetic-field generating coils 5X-1 and 5X-2, and the guidance-magnetic-field generating coils 5X-1 and 5X-2 are connected in series. The guidance-magnetic-field generating coil driver 29Y and the guidance-magnetic-field generating coils 5Y-1 and 5Y-2, and the guidance-magnetic-field generating coil driver 29Z and the guidance-magnetic-field generating coils 5Z-1 and 5Z-2 are also connected in the same way.

Figure 9:
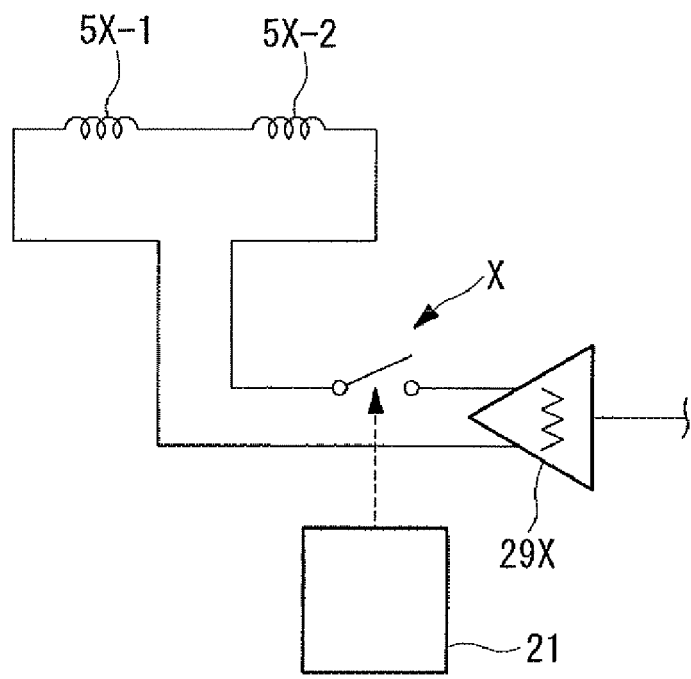
FIG. 9 is another circuit diagram showing the relationship between the guidance-magnetic-field generating coil and the guidance-magnetic-field generating coil driver in FIG. 7.

FIG. 9 is another circuit diagram showing the relationship between the guidance-magnetic-field generating coils and the guidance-magnetic-field generating coil drivers in FIG. 7. The basic configuration of the circuit diagram in FIG. 9 is the same as the circuit diagram in FIG. 8 but differs in that the switching units X, Y, and Z are further provided.

As shown in FIG. 9, the control signals from the control unit 21 are input to the switching units X, Y, and Z. The switching unit X constitutes a current circuit together with the guidance-magnetic-field generating coil driver 29X and the guidance-magnetic-field generating coils 5X-1 and 5X-2; the switching unit Y constitutes a current circuit together with the guidance-magnetic-field generating coil driver 29Y and the guidance-magnetic-field generating coils 5Y-1 and 5Y-2; and the switching unit Z constitutes a current circuit together with the guidance-magnetic-field generating coil driver 29Z and the guidance-magnetic-field generating coils 5Z-1 and 5Z-2.

The driver 31 moves a bed (not shown in the drawings) on which the subject 9 reclines. As shown in FIG. 6, the driver 31 moves the capsule medical device 3 together with the subject 9 by moving the bed on the basis of an output from the control unit 21.

Next, the operation of the capsule-medical-device guidance system 1 having the above configuration will be described.

First, an overview of the method of guiding the capsule medical device 3 in this embodiment will be given.

As shown in FIG. 6, the control unit 21 calculates control signals for forming the guidance magnetic field required to guide the capsule medical device 3 on the basis of the signal output from the operating unit 23. The calculated control signals are output to the respective signal generators 27X, 27Y, and 27Z, and the signal generators 27X, 27Y, and 27Z produce AC signals having prescribed waveforms on the basis of the control signals. The produced AC signals are output to the respective guidance-magnetic-field generating coil drivers 29X, 29Y, and 29Z, and the guidance-magnetic-field generating coil drivers 29X, 29Y, and 29Z current amplify the respective AC signals. The amplified AC signals are output to the respective guidance-magnetic-field generating coils 5X-1 and 5X-2, the guidance-magnetic-field generating coils 5Y-1 and 5Y-2, and the guidance-magnetic-field generating coils 5Z-1 and 5Z-2, and the guidance-magnetic-field generating coils 5X-1 and 5X-2, the guidance-magnetic-field generating coils 5Y-1 and 5Y-2, and the guidance-magnetic-field generating coils 5Z-1 and 5Z-2 form magnetic field components associated with the X-axis, Y-axis, and Z-axis directions in the respective guidance magnetic fields.

The control unit 21 can form a prescribed rotating magnetic field (guidance magnetic field) in the control area 17 by controlling the magnetic field intensities of the magnetic field components associated with the X-axis, Y-axis, and Z-axis directions of the guidance magnetic field formed by the guidance-magnetic-field generating coils 5X-1 and 5X-2, the guidance-magnetic-field generating coils 5Y-1 and 5Y-2, and the guidance-magnetic-field generating coils 5Z-1 and 5Z-2 (see FIG. 3) In other words, the control unit 21 can control the position and orientation of the rotational center axis of the above-described rotating magnetic field, as well as the rotating direction, the degree of rotation, and so forth of the above-described rotating magnetic field.

As shown in FIG. 1, the capsule medical device 3 disposed inside the control area 17 is rotationally driven by application of a rotational torque due to the permanent magnet 11 installed inside and the above-described rotating magnetic field. The position and rotational axis direction of the capsule medical device 3, as well as the rotating direction and the degree of rotation, are controlled by the above-described magnetic field.

The helical section 13 of the capsule medical device 3 converts the rotational torque applied by the above-described rotating magnetic field to a propulsive force by utilizing friction with the exterior thereof. The capsule medical device 1 is driven by the propulsive force converted by the helical section 13. The propulsive force acts in a direction parallel to the rotational axis direction of the capsule medical device 3, and the direction in which the propulsive force acts is controlled by the rotating direction of the above-described rotating magnetic field. The method of propelling and guiding the capsule medical device 3 with the above-described rotating magnetic field is substantially the same as the method disclosed in Japanese Unexamined Patent Application, Publication No. 2004-255174.

Next, an overview of the method of detecting the position of the capsule medical device 3 during observation of the subject 9 in this embodiment will be given.

First, as shown in FIG. 5, the capsule medical device 3 is introduced into the subject 9. At this time, the capsule medical device is not yet inside the control area 17. As shown in FIG. 1, from this state, the metal sensors 7Y-1 and 7Y-2 can detect entry of the capsule medical device 3 (metal portion) into the control area 17. Specifically, the metal sensor 7Y-1 can detect that the capsule medical device 3 enters the control area 17 from the positive direction on the Y-axis. The metal sensor 7Y-2 can detect that the capsule medical device 3 enters the control area 17 from the negative direction on the Y-axis. The capsule medical device 3 cannot be guided by the guidance magnetic field until the capsule medical device 3 enters the control area 17. Therefore, until the capsule medical device 3 enters the control area 17, the capsule medical device 3 is moved inside the control area 17 by moving the subject 9 or by moving the coil unit 5, or the like.

As described above, when the capsule medical device 3 enters the control area 17, guidance of the capsule medical device 3 by the guidance magnetic field commences, and observation, treatment, etc. is performed by the capsule medical device 3.

Next, the control method in a case where the capsule medical device 3 goes outside the control area 17, or is about to go outside, which is a feature of this embodiment, will be described.

Figure 10:
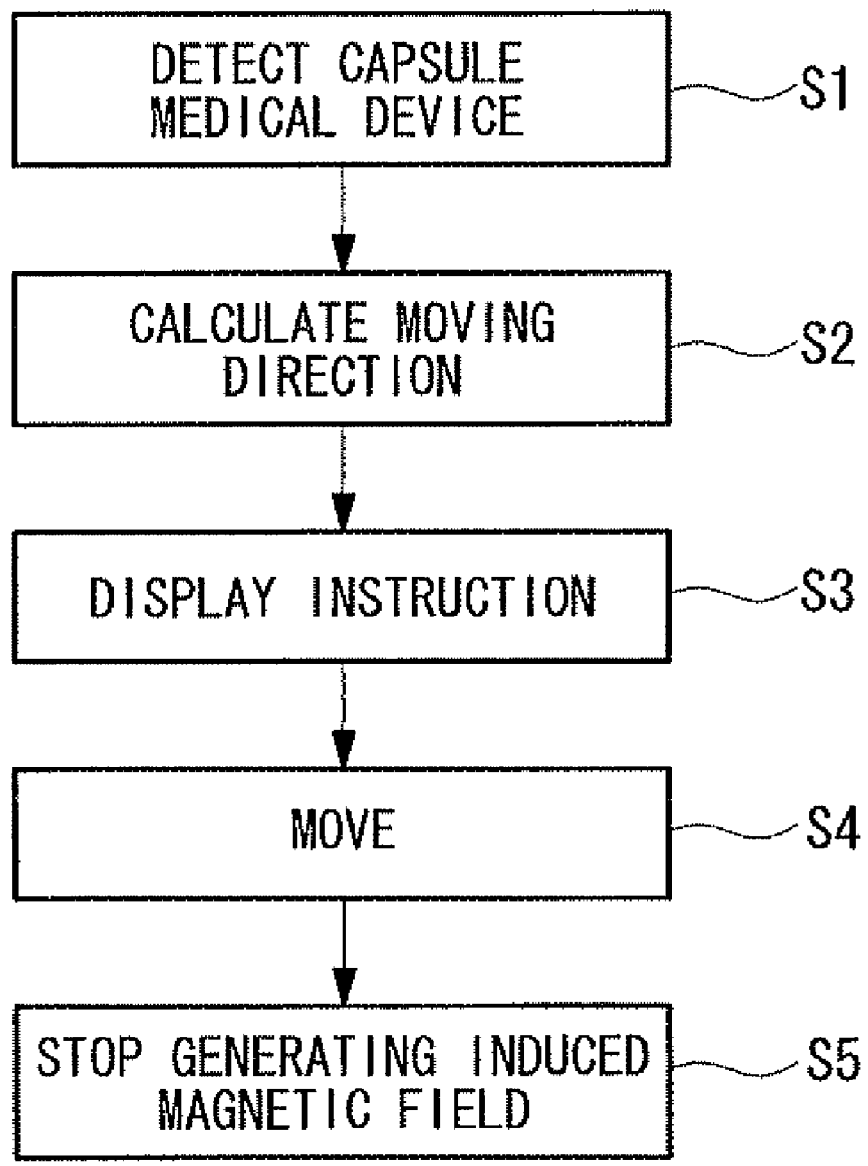
FIG. 10 is a flowchart for explaining control in the capsule medical device system in FIG. 6.

FIG. 10 is a flowchart for explaining control in the capsule medical device system in FIG. 6.

In some cases, if the moving distance of the capsule medical device 3 becomes large, the capsule medical device 3 may move outside the control area 17. Here, a description is given applied to a case where the capsule medical device 3 moves towards the anus of the subject 9 (the negative direction on the Y-axis in FIG. 1). When the capsule medical device 3 moves to the end of the control area 17 or goes outside the control area 17, the metal sensor 7Y-2 detects position information of the capsule medical device 3 (detection step) (Step S1).

The detection signal from the metal sensor 7Y-2 is input to the computational unit 35, as shown in FIG. 6. The computational unit 35 determines that the capsule medical device 3 is about to go outside the control area 17 in the negative direction on the Y-axis. The computational unit 35 calculates the direction for returning the capsule medical device 3 inside the control area 17 on the basis of the determination result. In this embodiment, because the capsule medical device 3 moves inside the control area 17 by moving the capsule medical device 3, the direction for returning the capsule medical device 3 inside the control area 17 is the positive direction on the Y-axis (calculation step) (step S2).

When the capsule medical device 3 moves inside the control area 17 by moving the control area 17, the direction for returning the capsule medical 3 inside the control area 17 is the negative direction on the Y-axis.

Based on the calculation result from the computational unit 35, the control unit 21 shows an instruction for moving the subject 9 on the display unit 25 (display step) (step S3) and moves the subject 9 by controlling the driver 31 (moving step) (step S4). The fact that the capsule-medical-device guidance system 1 has stopped in an error condition is also displayed on the display unit 25. Then, the control unit 21 outputs a signal for stopping generation of the guidance magnetic field (stopping step) (step S5).

Specifically, an instruction stating "Please move the subject 9 in the positive direction on the Y-axis" is displayed on the display unit 25. As described above, only the moving direction of the subject 9 may be displayed on the display unit 25, but it is not particularly limited thereto; in addition to the moving direction, the moving distance may also be displayed.

In this embodiment, an instruction is displayed on the display unit 25, and in addition, the control unit 21 moves the subject 9 by automatically controlling the driver 31. However, it is not particularly limited thereto; the operator may control the driver based on the instruction displayed on the display unit 25.

As described above, the subject 9 may be moved by the driver 31, but it is not particularly limited thereto; the subject 9 himself/herself may move.

The two methods described below are given as concrete examples of the method of stopping generation of the guidance magnetic field.

In the first method, as shown in FIG. 6, the output of the AC signal output from the signal generators 27X, 27Y, and 27Z is set to 0 V under the control of the control unit 21. For example, when the capsule medical device 3 goes outside the control area 17, the control unit 21 controls the output voltage of the AC signal output from the signal generator 27X to 0 V on the basis of the output from the computational unit 35. In this case, the output voltage of the AC signal remains at 0 V, even though it is current amplified in the guidance-magnetic-field generating coil driver 29X. Therefore, the flow of electrical current from the guidance-magnetic-field generating coil driver 29X to the guidance-magnetic-field generating coils 5X-1 and 5X-2 is stopped, and generation of the guidance magnetic field from the guidance-magnetic-field generating coils 5X-1 and 5X-2 is stopped.

In the second method, as shown in FIG. 7, the outputs from the guidance-magnetic-field generating coil drivers 29X, 29Y, and 29Z are turned OFF (stopped) under the control of the control unit 21. This method involves blocking the current path formed by the guidance-magnetic-field generating coil driver 29X and the guidance-magnetic-field generating coils 5X-1 and 5X-2 by, for example, turning off switches of the switching units X, Y, and Z provided at an output of the guidance-magnetic-field generating coil driver 29X. When the capsule medical device 3 is inside the control area 17, the output of the switch is turned ON. In other words, the output of the guidance-magnetic-field generating coil driver 29X is directly input to the guidance-magnetic-field generating coils 5X-1 and 5X-2. When the capsule medical device 3 goes outside the control area 17, the output of the switch is turned OFF. In other words, the output from the guidance-magnetic-field generating coil driver 29X is not input to the guidance-magnetic-field generating coils 5X-1 and 5X-2.

More specifically, the computational unit 35 determines that the capsule medical device 3 goes outside the control area 17 on the basis of the detection signals input from the metal sensors 7Y-1 and 7Y-2. If so, the control unit 21 turns the output of the guidance-magnetic-field generating coil driver 29X OFF on the basis of the output from the computational unit 35. In other words, by blocking the current path to stop the flow of current flowing from the guidance-magnetic-field generating coil driver 29X to the guidance-magnetic-field generating coils 5X-1 and 5X-2, generation of the guidance magnetic field from the guidance-magnetic-field generating coils 5X-1 and 5X-2 is stopped. In this case, even though the AC signal is output from the signal generator 27X, it is possible to stop generation of the guidance magnetic field. Therefore, it is possible to easily stop generation of the guidance magnetic field from the guidance-magnetic-field generating coil driver 29X.

The method of stopping generation of the guidance magnetic field is not limited to the two methods described above. It is possible to stop generation of the guidance magnetic field by combining the two methods described above.

The capsule medical device 3 moves towards the center of the control area 17 by moving the subject 9 in the positive direction on the Y-axis. When the capsule medical device 3 enters the control area 17, the distance between the metal sensor 7Y-2 and the capsule medical device 3 is increased, and the metal sensor 7Y-2 gives no response (gives no output).

The computational unit 35 determines that the capsule medical device 3 has entered the control area 17 based on the fact that there is no output from the metal sensor 7Y-2. Based on the determination by the computational unit 35, the control unit 21 removes the instruction displayed on the display unit 25 and resumes generating the guidance magnetic field. More specifically, with the first method of stopping generation of the guidance magnetic field described above, the voltages of the AC signals output from the signal generators 27X, 27Y, and 27Z which are forcedly set to 0 V are set back to the prescribed waveforms required for generating the guidance magnetic field. With the second method of stopping generation of the guidance magnetic field described above, the switch provided at the output etc. of the guidance-magnetic-field generating coil driver 29X is on, thus turning the output ON. In other words, the blocked current path etc. formed by the guidance-magnetic-field generating coil driver 29X and the guidance-magnetic-field generating coils 5X-1 and 5X-2 is connected.

According to the above, the capsule medical device 3 returns to the control area 17, and guidance of the capsule medical device 3 by the guidance magnetic field is continued.

As described above, the metal sensors 7Y-1 and 7Y-2 may be used for position detection of the capsule medical device 3, but it is not particularly limited thereto; instead of the metal sensors 7Y-1 and 7Y-2, an ultrasonic sensor (detection unit) may be used. With this configuration, as the object to be detected by the ultrasonic sensor, instead of the metal portion, it is preferable to provide a member (detected portion) that reflects ultrasonic waves in the capsule medical device 3.

With this configuration, the ultrasonic sensor may be placed on the surface of the subject 9 to detect the position of the capsule medical device 3 inside the body cavity of the subject 9. The location at which the ultrasonic sensor is placed can be determined, for example, on the basis of the distance from the guidance-magnetic-field generating coils 5. Regarding the instruction for positional placement of the ultrasonic sensor, it is possible to aim at the irradiation point of a laser pointer irradiating the subject 9.

With the configuration described above, because the coil unit 5, the metal sensors 7Y-1 and 7Y-2, and the control unit 21 are provided, it is possible to easily prevent the capsule medical device 3 from deviating a great distance from the control area 17.

Because the coil unit 5 forms the guidance magnetic field for guidance control of the capsule medical device 3 inside the control area 17, it is possible to guide the capsule medical device 3 located inside the control area 17 in a prescribed direction. The metal sensors 7Y-1 and 7Y-2 can detect the capsule medical device 3 going outside the control area 17, that is, the capsule medical device 3 inside the control area 17 moving excessively outside the control area 17, and it is thus possible to prevent an inability to perform guidance control of the capsule medical device 3. At the same time, the metal sensors 7Y-1 and 7Y-2 can output a signal indicating that the capsule medical device 3 has gone outside the control area 17. Because the control unit 21 can stop forming the guidance magnetic field by controlling the coil unit 5, it is possible to easily prevent the capsule medical device 3 from deviating a great distance from the control area 17. In other words, because formation of the guidance magnetic field is stopped, the force acting on the capsule medical device 3 due to the guidance magnetic field vanishes, and it is possible to relatively move the capsule medical device 3 and the control area 17 to easily move the capsule medical device 3 inside the control area 17. In addition, because guidance control of the capsule medical device 3 by the guidance magnetic field is also stopped, it is possible to prevent the capsule medical device 3 from going farther away from the control area 17 due to an erroneous operation.

Because the computational unit 35 and the display unit 25 are provided, it is possible to easily prevent the capsule medical device 3 from deviating a great distance from the control area 17.

Because the computational unit 35 is provided, it is possible to computationally determine the direction for returning the capsule medical device 3 to the control area 17, and it is thus possible to easily prevent the capsule medical device 3 from deviating a great distance from the control area 17. Because the display unit 25 is provided, the operator mentioned above can easily find the direction for returning the capsule medical device 3 to the control area 17, and it is thus possible to easily prevent the capsule medical device 3 from deviating a great distance from the control area 17.

Because the driver 31 is provided, it is possible to easily prevent the capsule medical device 3 from deviating a great distance from the control area 17 that is suitable for guidance control of the capsule medical device 3.

The driver 31 moves the subject 9 in which the capsule medical device 3 is introduced. As a result, it is possible to return the capsule medical device 3 inside the control area 17. Because the driver 31 automatically moves the subject 9 on the basis of the outputs from the metal sensors 7Y-1 and 7Y-2, it is possible to easily prevent the capsule medical device 3 from deviating a great distance from the control area 17 compared to a method in which the operator moves the capsule medical device 3 to return the capsule medical device 3 inside the control area 17.

Because the metal portion and the metal sensors 7Y-1 and 7Y-2 are provided, it is possible to detect that the capsule medical device 3 has gone outside the control area 17.

Because the metal portion is provided in the capsule medical device 3, it is possible to detect the position of the capsule medical device 3 by detecting the position of the metal portion. Because the metal sensors 7Y-1 and 7Y-2 are disposed in the vicinity of a boundary region of the control area 17, it is possible to easily prevent the metal portion, in other words, the capsule medical device 3, from going outside the control area 17.

Because the method of controlling the capsule medical device 3 in this embodiment is provided with Step S1, Step S2, Step S3, and Step S5, it is possible to easily prevent the capsule medical device 3 from deviating a great distance from the control area 17.

By providing Step S1, it is possible to detect that the capsule medical device 3 has gone outside the control area 17, and it is thus possible to prevent an inability to perform guidance control of the capsule medical device 3. By providing Step S2, it is possible to calculate the direction for returning the capsule medical device 3 to the control area 17, and it is thus possible to easily prevent the capsule medical device 3 from deviating a great distance from the control area 17. By providing Step S3, for example, the operator of the capsule-medical-device guidance system 1 can easily find the direction for returning the capsule medical device 3 to the control area 17, and it is thus possible to prevent the capsule medical device from deviating a great distance from the control area 17. By providing Step S5, formation of the guidance magnetic field is stopped, and it is thus possible to easily prevent the capsule medical device 3 from deviating a great distance from the control area 17. In other words, the force acting on the capsule medical device due to the guidance magnetic field vanishes, and it is possible to relatively move the capsule medical device 3 and the control are 17 to easily move the capsule medical device 3 inside the control area 17. Furthermore, because guidance control of the capsule medical device 3 by the guidance magnetic field is also stopped, it is possible to prevent the capsule medical device 3 from going farther away from the control area 17 due to an erroneous operation.

Because Step S4 is provided, it is possible to easily prevent the capsule medical device 3 from deviating a great distance from the control area 17.

Because Step S4 is provided, the capsule medical device 3 advances, by a prescribed amount, in the direction for returning to the control area 17. Therefore, guidance control of the capsule medical device 3 becomes easier in subsequent handling, and it is thus possible to easily prevent the capsule medical device from deviating a great distance from the control area 17. At the same time, because the distance moved is restricted to a prescribed amount, the capsule medical device 3 does not move to a position away from a position outside the control area. Therefore, the operator of the capsule medical device 3 can easily find the position of the capsule medical device 3, and it is possible to easily prevent the capsule medical device 3 from deviating a great distance from the control area 17.

Second Embodiment

Next, a second embodiment of the present invention will be described with reference to FIG. 11 and FIG. 12.

The basic configuration of the capsule-medical-device guidance system of this embodiment is the same as that of the first embodiment, but a structure for detecting the position of the capsule medical device differs from that in the first embodiment. Therefore, only the vicinity of the structure for detecting the position of the capsule medical device will be described using FIG. 11 and FIG. 12, and a description of other structures etc. will be omitted.

Figure 11:
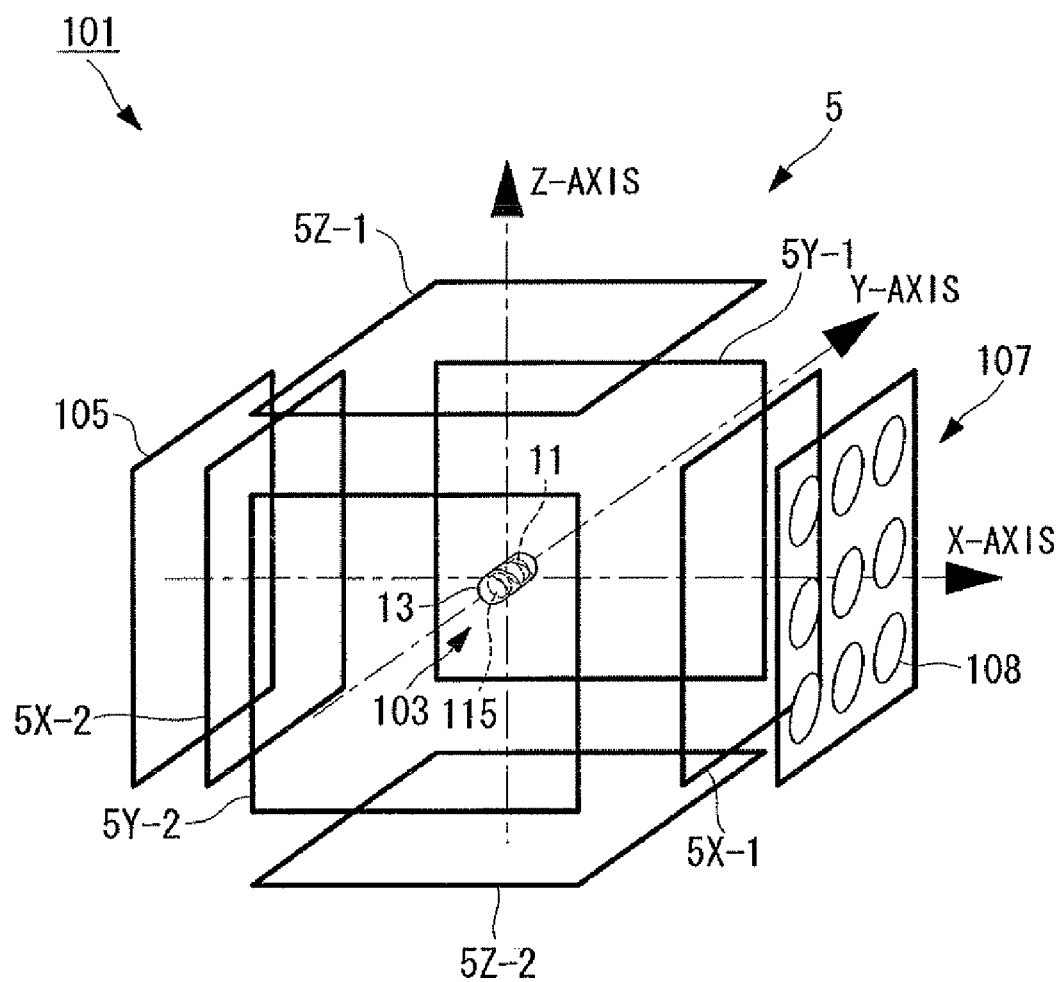
FIG. 11 is a diagram for explaining the external configuration of a capsule-medical-device guidance system in a second embodiment of the present invention.

FIG. 11 is a diagram for explaining the external configuration of the capsule-medical-device guidance system in this embodiment.

Elements that are identical to those in the first embodiment are assigned the same reference numerals, and a description thereof is omitted.

Figure 12:
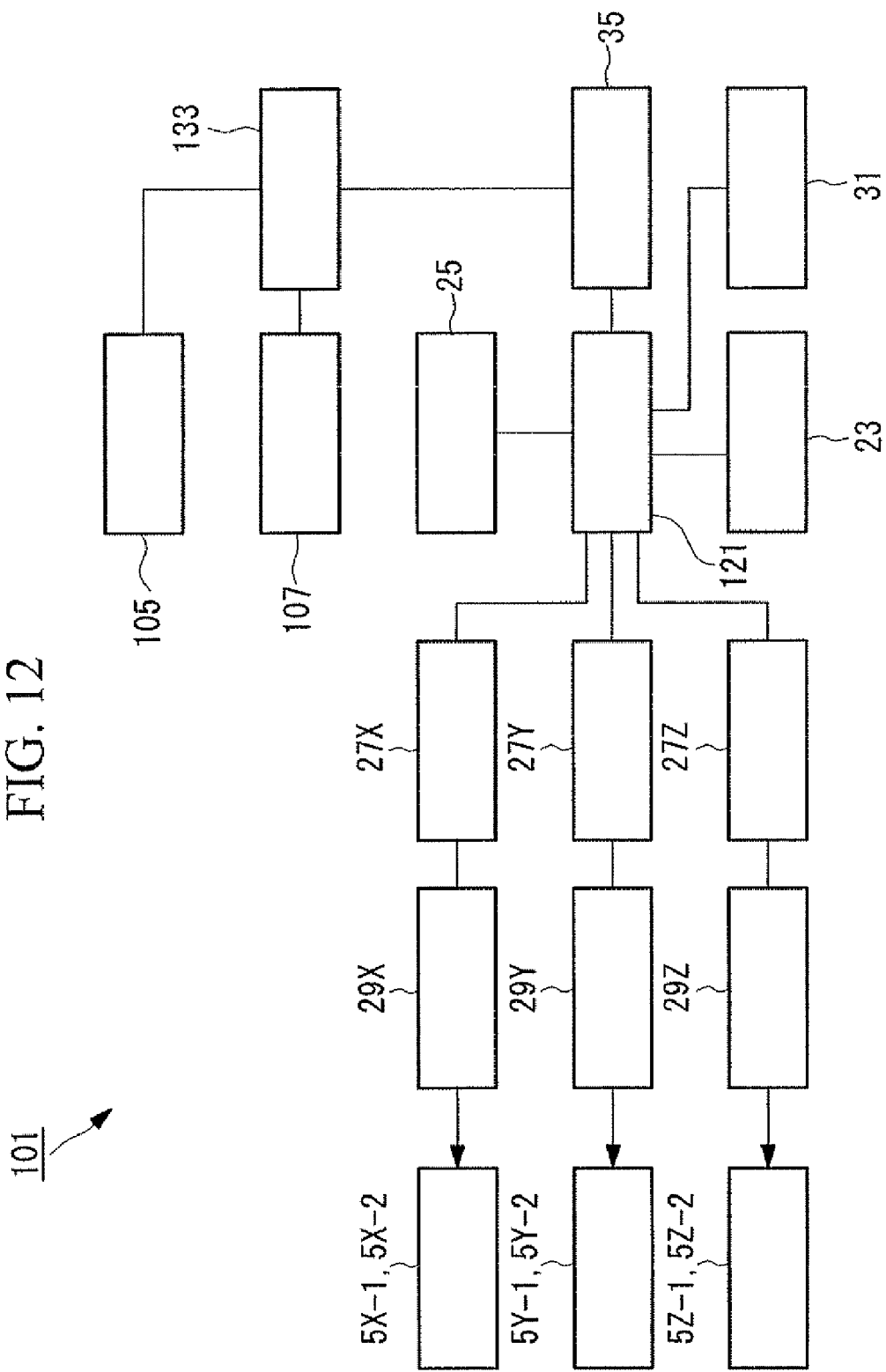
FIG. 12 is a block diagram for explaining the circuit configuration in the capsule-medical-device guidance system in FIG. 11.

As shown in FIG. 11, a capsule-medical-device guidance system (medical-device guidance system) 101 includes a capsule medical device (medical device) 103 which is introduced into a subject etc.; a coil unit 5 which forms a guidance magnetic field; a position-detection-magnetic-field generating coil (position-detection-magnetic-field forming unit, detection unit) 105 used in position detection of the capsule medical device 103; a magnetic-field detection unit (detection unit) 107; a position calculating unit 133 (detection unit); and a memory 135 (see FIG. 12).

The capsule medical device 103 is guided inside a tract in the body cavity of the subject 9 in order to perform a medical procedure, such as observation, diagnosis, or treatment, of an inner surface of the gastrointestinal tract. As shown in FIG. 11, the capsule medical device 103 is provided with a permanent magnet (magnet) 11, a helical section 13, and a magnetic induction coil 115. Magnetic induction is brought about in the magnetic induction coil 115 due to a position-detection magnetic field applied from the outside. Adding a capacitor (condenser) to the magnetic induction coil 115 forms a resonance circuit in which resonance is brought about at a prescribed frequency. A resonance circuit may be formed by adding a capacitor to the magnetic induction coil 115, as described above, but it is not particularly limited thereto; a resonance circuit may be formed by parasitic capacitance of the magnetic induction coil 115 itself.

The position-detection-magnetic-field generating coil 105 forms the position-detection magnetic field inside a control area 17. As shown in FIG. 11, the position-detection-magnetic-field generating coil 105 is disposed farther towards the positive direction on the X-axis than the guidance-magnetic-field generating coil 5X-2. The position-detection-magnetic-field generating coil 105 forms the position-detection magnetic field on the basis of an AC signal supplied from the position calculating unit 133 (see FIG. 12).

The magnetic-field detection unit 107 detects the induced magnetic field formed in the magnetic induction coil 115 and the position-detection magnetic field formed by the position-detection-magnetic-field generating coil 105. As shown in FIG. 11, the magnetic-field detection unit 107 is disposed farther towards the positive direction on the X-axis than the guidance-magnetic-field generating coil 5X-1. A plurality (nine in this embodiment) of sense coils 108 are provided in the magnetic-field detection unit 107, and a induced magnetic field and the position-detection magnetic field are detected by the sense coils 108.

FIG. 12 is a block diagram for explaining the circuit configuration in the capsule-medical-device guidance system in FIG. 11.

As shown in FIG. 12, the capsule-medical-device guidance system 101 further includes a control unit 121, an operating unit 23, a display unit 25, signal generators 27X, 27Y, and 27Z, guidance-magnetic-field generating coil drivers 29X, 29Y, and 29Z, a driver 31, and a computational unit 35.

The control unit 121 controls the formation of the guidance magnetic field on the basis of an output from the computational unit 35. The computational unit 35 judges that the capsule medical device 103 has gone outside the control area 17 on the basis of an output from the position calculating unit 133. A memory is provided in the computational unit 35. The memory stores the output of the magnetic-field detection unit 107 when only the position-detection magnetic field is applied to the magnetic-field detection unit 107.

The position calculating unit 133 forms the position-detection magnetic field by controlling the position-detection-magnetic-field generating coil 105. The position calculating unit 133 outputs an AC signal to the position-detection-magnetic field generating coil 105, and a magnetic-field detection signal is input thereto from the magnetic-field detection unit 107. Also, the position calculating unit 133 outputs the input magnetic field detection signal to the computational unit 35.

First, the operation of the capsule-medical-device guidance system 101 having the above configuration will be described.

The method of guiding the capsule medical device 103 in this embodiment is roughly the same as that in the first embodiment, and a description thereof is thus omitted.

Next, an overview of the method of detecting the position of the capsule medical device 103 in this embodiment will be described.

When detecting the position of the capsule medical device 103, as shown in FIG. 12, an AC current is output to the position-detection magnetic-field generating coil 105 from the position calculating unit 133. The frequency of the AC current is substantially equal to the resonance frequency of the resonance circuit containing the magnetic induction coil 115. As shown in FIG. 11, the position-detection magnetic-field generating coil 105 generates a position-detection magnetic field. When the capsule medical device 103 is located inside the control area 17, the position-detection magnetic field is applied to the magnetic induction coil 115. The magnetic induction coil 115 forms an induced magnetic field due to the position-detection magnetic field. The position-detection magnetic field and the induced magnetic field are applied to the sense coil 108 in the magnetic-field detection unit 107, and a position detection signal, which is a voltage signal containing voltage components associated with the position-detection magnetic field and the induced magnetic field, is output from the sense coils 108.

The position detection signal is input to the computational unit 35 via the position calculating unit 133. The position calculating unit 133 extracts a voltage signal associated with only the induced magnetic field from the position detection signal on the basis of the voltage signal associated with only the position-detection magnetic field stored in advance in the memory in the computational unit 35. The position calculating unit 133 further calculates the position of the magnetic induction coil 115, that is, the position of the capsule medical device 103, on the basis of the extracted voltage signal. The method of detecting the position of the capsule medical device 103 with the induced magnetic field described above is substantially the same as the method disclosed in "High-precision position detection system using an LC-resonant magnetic marker", Journal of the Magnetics Society of Japan, 29, 153-156 (2005).

Based on the position of the capsule medical device 103 calculated by the position calculating unit 133, the computational unit 35 determines whether the capsule medical device 103 is located inside the control area 17, or whether it is located outside, using one of the two methods below.

The first method is the method used when the relative positional relationship between the control area 17 and the magnetic-field detection unit 107 is known, and when the relative position of the control area 17 with respect to the magnetic-field detection unit 107 is stored in the memory in the computational unit 35. Specifically, it is the method used when the relative positional relationship between the coil unit 5 and the magnetic-field detection unit 107 is known.

For example, when the range of the control area 17 is represented by a cuboid defined by upper bounds and lower bounds on the X-axis, Y-axis, and Z-axis, these upper bounds and lower bounds are stored in the memory in the computational unit 35. The computational unit 35 compares coordinates representing the calculated position of the capsule medical device 103 with the upper bounds and lower bounds described above. If a coordinate value of the capsule medical device 103 exceeds either one of the bounds, i.e., the upper bound or the lower bound, it is judged that the capsule medical device 103 has gone outside the control area 17. Also, can be judged in which direction the capsule medical device 103 has gone outside the control area 17 based on which coordinate value, i.e., the X coordinate value, the Y coordinate value, or the Z coordinate value, of the capsule medical device 103 exceeds which bound, i.e., the upper bound or the lower bound.

The second method is the method used when the relative positional relationship between the control area 17 and the magnetic-field detection unit 107 is not known. Specifically, it is the method used when the relative positional relationship between the coil unit 5 and the magnetic-field detection unit 107 is not known. In such a case, the control unit 121 finds the relative positional relationship between the control area 17 and the magnetic-field detection unit 107 by obtaining in advance the position of a common reference point of the control area 17 and the magnetic-field detection unit 107.

For example, the position of a common reference point of the control area 17 and the magnetic-field detection unit 107 is obtained by disposing the capsule medical device 103, or something that generates the same magnetic field as the capsule medical device 103, at the center of the control area 17 and detecting the induced magnetic field etc. with the magnetic-field detection unit 107. Accordingly, the position calculating unit 133 can determine the relative position at the center of the control area 17 with respect to the magnetic-field detection unit 107, and at the same time, can determine the upper bounds and lower bounds of the control area 17 in the X-axis, Y-axis, and Z-axis directions with respect to the magnetic-field detection unit 107. Additionally, with this embodiment, because the computational unit 35 can also detect the orientation of the capsule medical device 103, it can perform a coordinate transformation between the control area 17 (coil unit 5) and the magnetic-field detection unit 107.

After finding the relative positional relationship between the control area 17 and the magnetic-field detection unit 107, similarly to the first method described above, it is possible to judge whether the capsule medical device 103 has gone outside the control area 17.

The control method subsequent to (from Step S3 in FIG. 6) the capsule medical device 103 being outside, or being about to go outside, the control area 17 is the same as in the first embodiment, and therefore, a description thereof is omitted.

With the configuration described above, because the capsule medical device 103 is provided with the magnetic induction coil 115, and because the position-detection-magnetic-field generating coil 105, the magnetic-field detection unit 107, and the computational unit 35 are provided, the computational unit 35 can judge that the capsule medical device 103 has gone outside the control area 17.

Because the capsule medical device 103 is provided with the magnetic induction coil 115, by applying the position-detection magnetic field, it is possible to generate an induced magnetic field from the capsule medical device 103 (the magnetic induction coil 115). Because the capsule-medical-device guidance system 101 is provided with the position-detection-magnetic-field generating coil 105, it is possible to form the position-detection magnetic field in the control area 17 and to generate an induced magnetic field from the capsule medical device 103 positioned inside the control area 17. The magnetic-field detection unit 107 can obtain an output signal, according to the strength of the induced magnetic field, received from the magnetic-field detection unit 107. The position calculating unit 133 can calculate at which position the capsule medical device 103 is located, with respect to the magnetic-field detection unit 107, on the basis of the output signal from the magnetic-field detection unit 107. The computational unit 35 can judge whether the capsule medical device 103 has gone outside the control area 17 on the basis of the above-mentioned calculation result.

First Modification of Second Embodiment

A first modification of the second embodiment of the present invention will be described next with reference to FIG. 13 and FIG. 14.

The basic configuration of the capsule-medical-device guidance system of this modification is the same as the second embodiment, but the structure associated with position detection of the capsule medical device differs from that in the second embodiment. Therefore, only the vicinity of the structure associated with position detection of the capsule medical device will be described using FIG. 13 and FIG. 14, and a description of other structures etc. will be omitted.

Figure 13:
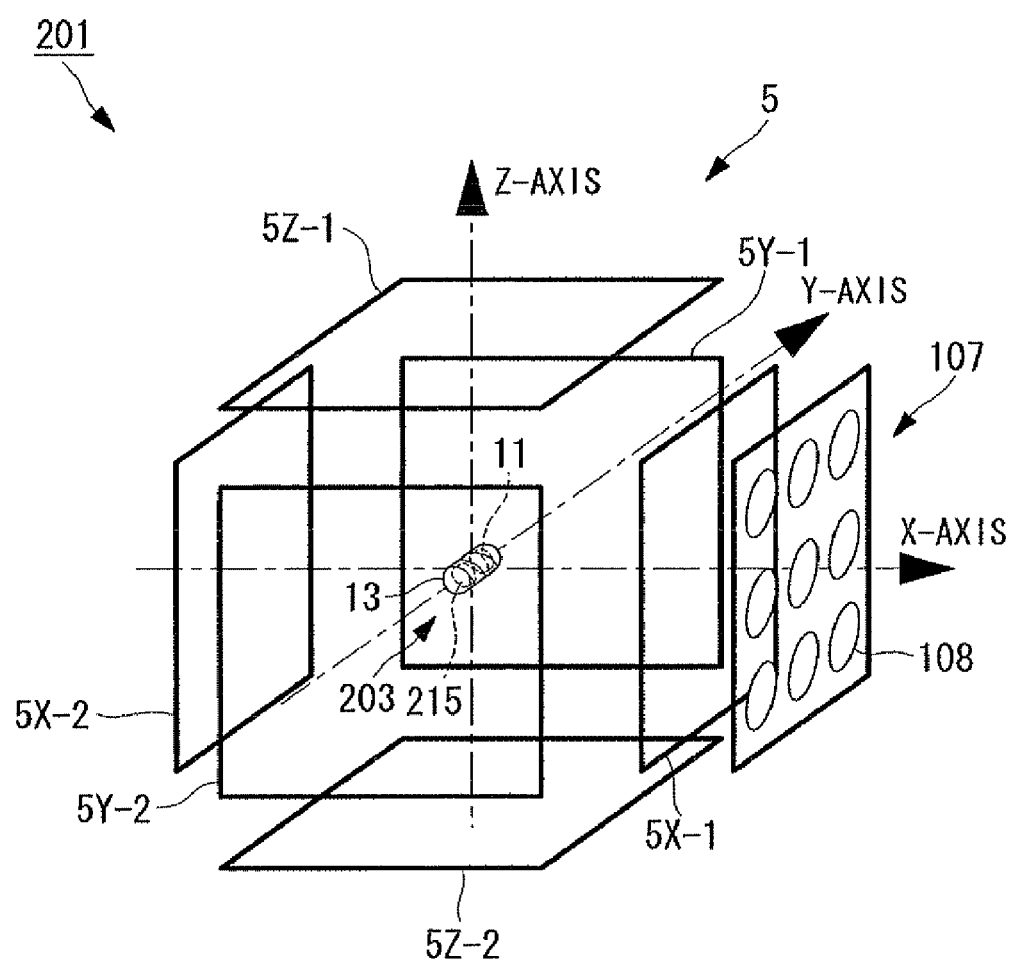
FIG. 13 is a diagram for explaining the external configuration of a capsule-medical-device guidance system in a first modification of the second embodiment of the present invention.

FIG. 13 is a diagram for explaining the external appearance of the capsule-medical-device guidance system in this modification.

Elements that are identical to those in the second embodiment are assigned the same reference numerals, and a description thereof is omitted.

Figure 14:
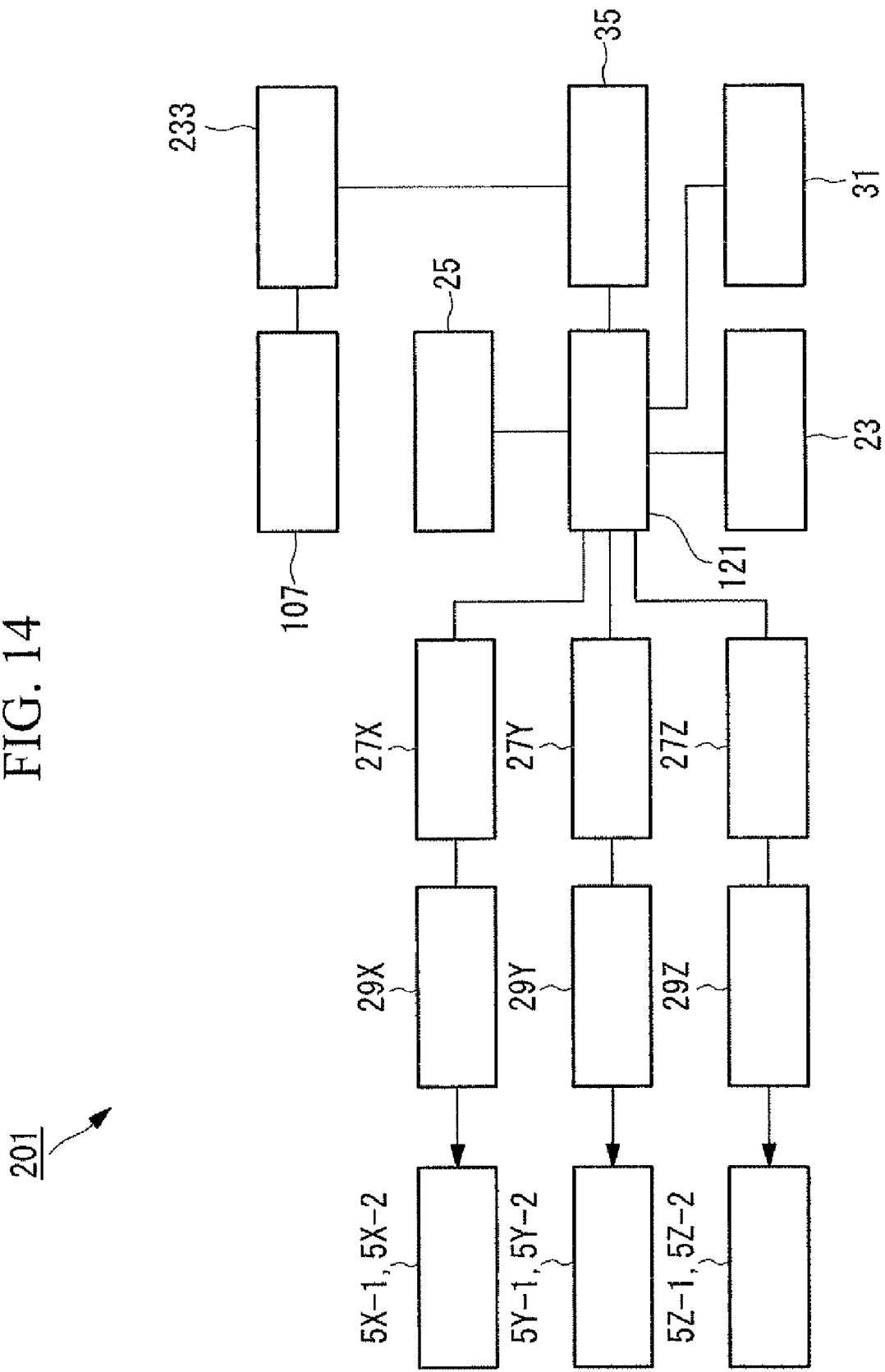
FIG. 14 is a block diagram for explaining the circuit configuration in the capsule-medical-device guidance system in FIG. 13.

As shown in FIG. 13, a capsule-medical-device guidance system (medical-device guidance system) 201 includes a capsule medical device (medical device) 203 which is introduced into a subject etc., a coil unit 5 forming a guidance magnetic field, a magnetic-field detection unit 107 used for position detection of the capsule medical device 203, and a position calculating unit 233 (detection unit) (see FIG. 14).

The capsule medical device 203 is guided inside a tract in the body cavity of the subject 9 in order to perform a medical procedure, such as observation, diagnosis, or treatment, of an inner surface of the gastrointestinal tract. As shown in FIG. 13, the capsule medical device 203 is provided with a permanent magnet 11, a helical section 13, and a magnetic-field generator 215. The magnetic-field generator 215 generates its own magnetic field directed outside. The magnetic-field generator 215 includes a coil and an oscillator circuit; an AC signal output from the oscillator circuit is supplied to the coil, and a magnetic field is formed by the coil.

FIG. 14 is a block diagram for explaining the circuit configuration in the capsule-medical-device guidance system in FIG. 13.

As shown in FIG. 14, the capsule-medical-device guidance system 201 further includes a control unit 121, an operating unit 23, a display unit 25, signal generators 27X, 27Y, and 27Z, guidance-magnetic-field generating coil drivers 29X, 29Y, and 29Z, and a driver 31.

A magnetic-field detection signal is input to the position calculating unit 233 from the magnetic-field detection unit 107, and the input magnetic-field detection signal is output to a computational unit 35.

First, the operation of the capsule-medical-device guidance system 201 having the above configuration will be described.

The method of guiding the capsule medical device 203 in this embodiment is roughly the same as that in the first embodiment, and a description thereof is thus omitted.

Next, an overview of the method of detecting the position of the capsule medical device 203 in this embodiment will be described.

A magnetic field is formed by the magnetic-field generator 215 in the capsule medical device 203. The magnetic field is applied to sense coils 108 in the magnetic-field detection unit 107, and position detection signals, which are voltage signals associated with the above-described magnetic field, are output from the sense coils 108.

The position detection signal is input to the computational unit 35 via the position-calculating unit 233. The position calculating unit 233 calculates the position of the magnetic-field generator 215, in other words, the position of the capsule medical device 203, on the basis of the position detection signal.

Judgment etc. of whether the capsule medical device 203 has gone outside the control area 17 is the same as in the second embodiment, and therefore, a description thereof is omitted.

With the configuration described above, because the capsule medical device 203 is provided with the magnetic-field generator 215, it is not necessary to use a position-detection-magnetic-field generating coil or the like.

The magnetic-field generator 215 can form a magnetic field by itself. Therefore, the magnetic-field detection unit 107 can detect only the magnetic field that the magnetic-field generator 215 forms. For example, compared with a method in which a magnetic induction coil is provided in the capsule medical device, and the position etc. of the capsule medical device is detected using the induced magnetic field, it is not necessary to separate a voltage component associated with the position-detection magnetic field and a voltage component associated with the induced magnetic field, which components are contained in the position detection signal.

Second Modification of Second Embodiment

Next, a second modification of the second embodiment of the present invention will be described with reference to FIG. 15 and FIG. 16.

The basic configuration of the capsule-medical-device guidance system of this modification is the same as the first modification of the second embodiment, but the structure associated with position detection of the capsule medical device differs from that in the first modification. Therefore, only the vicinity of the structure for position detection of the capsule medical device will be described using FIG. 15 and FIG. 16, and a description of other structures etc. will be omitted.

Figure 15:
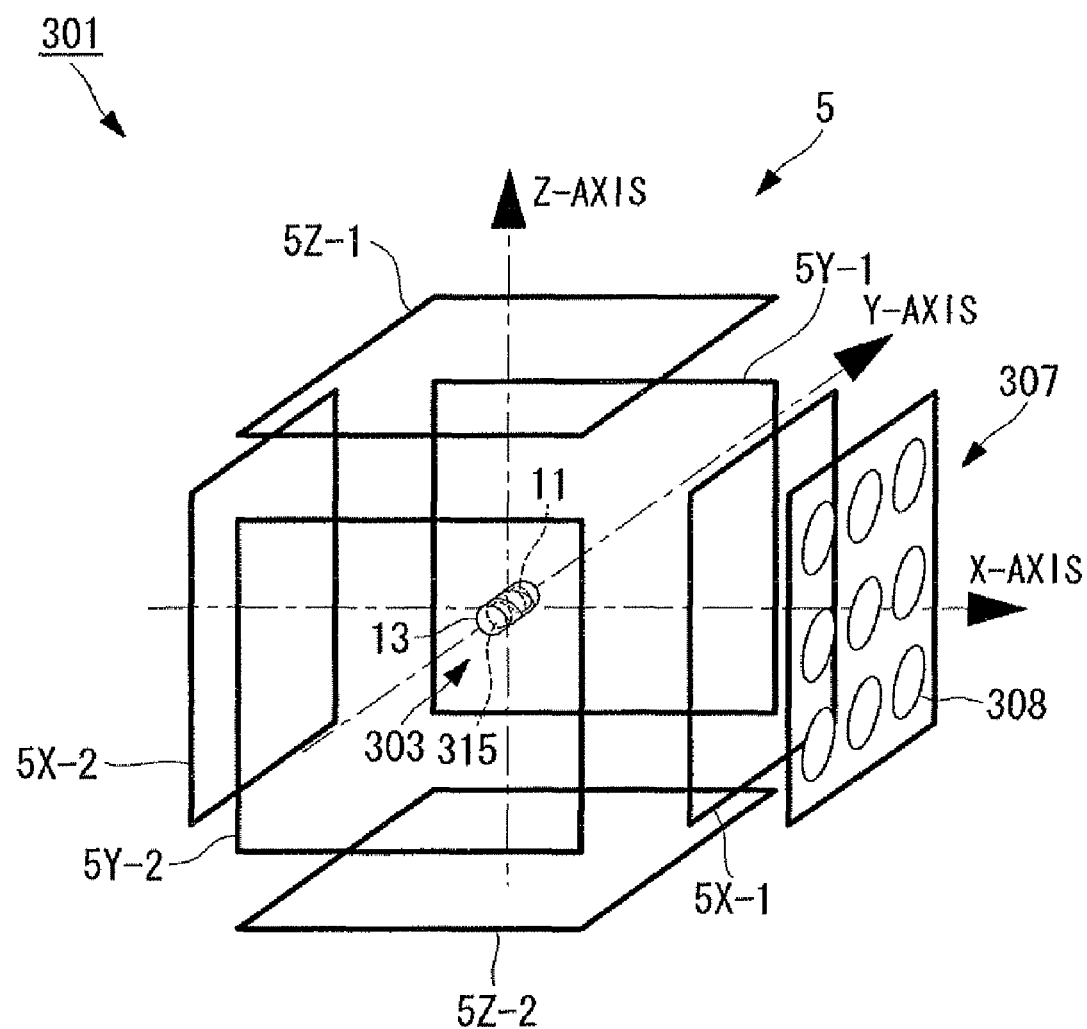
FIG. 15 is a diagram for explaining the external configuration of a capsule-medical-device guidance system in a second modification of the second embodiment of the present invention.

FIG. 15 is a diagram for explaining the outer appearance of the capsule-medical-device guidance system in this modification.

Elements that are identical to those in the second embodiment are assigned the same reference numerals, and a description thereof is omitted.

Figure 16:
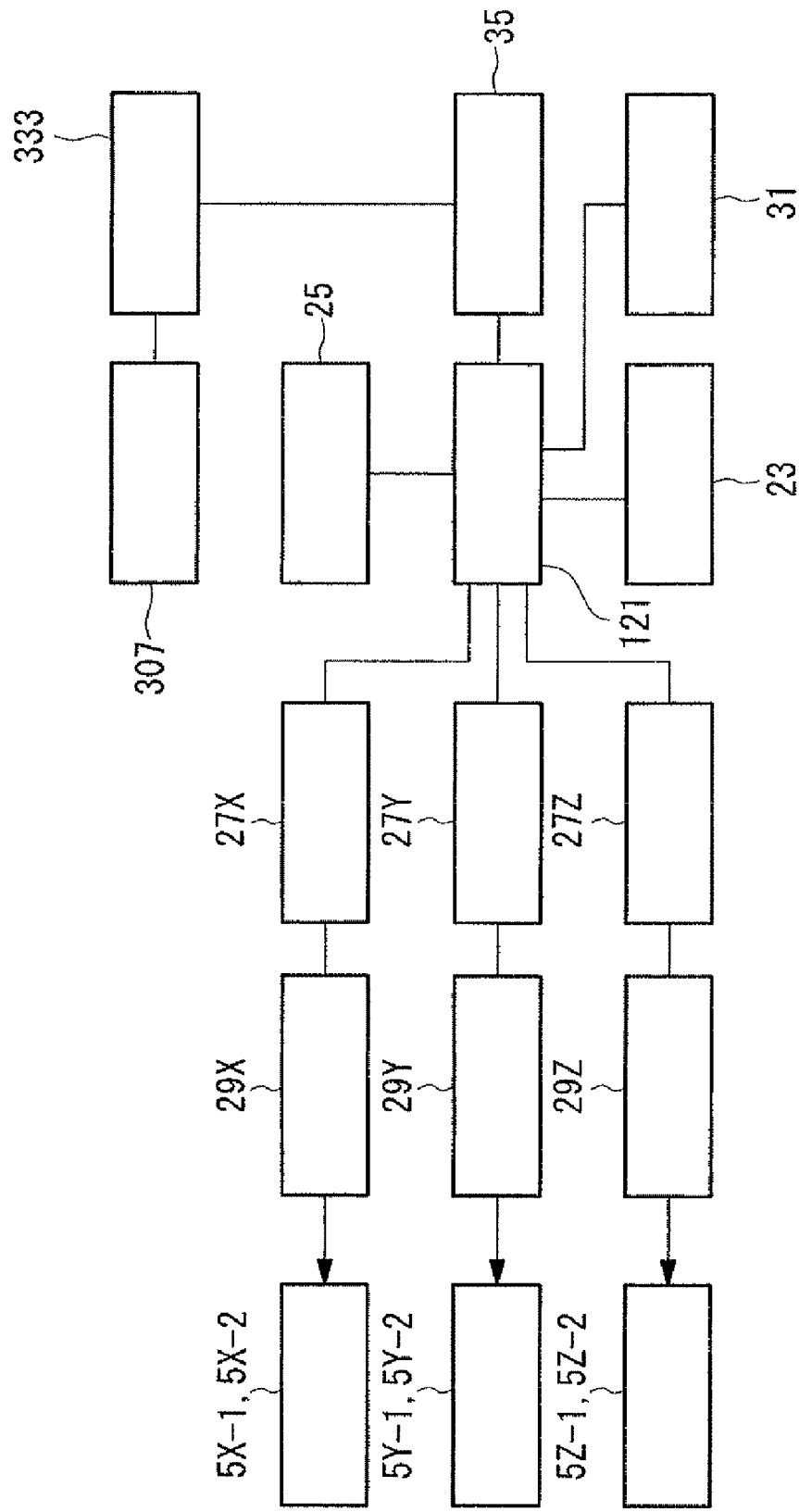
FIG. 16 is a block diagram for explaining the circuit configuration in the capsule-medical-device guidance system in FIG. 15.

As shown in FIG. 15, a capsule-medical-device guidance system (medical-device guidance system) 301 includes a capsule medical device (medical device) 303 which is introduced into a subject etc.; a coil unit 5 which forms a guidance magnetic field; a wireless reception unit (detection unit) 307 used in position detection of the capsule medical device 303; and a position calculating unit 333 (detection unit) (see FIG. 16).

The capsule medical device 303 is guided inside a tract in the body cavity of the subject 9 in order to perform a medical procedure, such as observation, diagnosis, or treatment, of an inner surface of the gastrointestinal tract. As shown in FIG. 15, the capsule medical device 303 is provided with a permanent magnet (magnet) 11, a helical section 13, and a wireless transmission unit 315. The wireless transmission unit 315 transmits radio waves directed outside. The radio waves are used to communicate between the capsule medical device 303 and the outside. For example, if the capsule medical device 303 is provide with an image acquisition unit, the above-mentioned radio waves can be used when transmitting acquired images to the outside.

The wireless reception unit 307 receives the radio waves transmitted from the wireless transmission unit 315. The wireless reception unit 307 is provided with a plurality (nine in this embodiment) of antennas (wireless reception units) 308, and the radio waves are received by the antennas 308.

FIG. 16 is a block diagram for explaining the circuit configuration in the capsule-medical-device guidance system in FIG. 15.

As shown in FIG. 16, the capsule-medical-device guidance system 301 further includes a control unit 121, an operating unit 23, a display unit 25, signal generators 27X, 27Y, and 27Z, guidance-magnetic-field generating coil drivers 29X, 29Y, and 29Z, and a driver 31.

The position calculating unit 333 selects the antenna 308 that receives the strongest signal (having the highest communication quality) from among the plurality of antennas 308 and uses the selected antenna 308 to continue communicating with the capsule medical device 303. The position calculating unit 333 then outputs the signal intensities of the respective radio waves in the plurality of antennas 308 to a computational unit 35.

Next, the operation of the capsule-medical-device guidance system 301 having the above configuration will be described.

First, because the method of guiding the capsule medical device 303 in this embodiment is roughly the same as that in the first embodiment, a description thereof is omitted.

Next, an overview of the method of detecting the position of the capsule medical device 303 in this embodiment will be described.

Radio waves are transmitted by the wireless transmission unit 315 in the capsule medical device 303. The plurality of antennas 308 in the wireless reception unit 307 receive the radio waves and output reception signals according to the intensities of the received radio waves. Regarding the position calculating unit 333, the received intensities of the radio waves in the respective antennas 308 are output to the position calculating unit 333. Based on the received intensities of the radio waves in the respective antennas 308, the position calculating unit 333 calculates the position of the wireless transmission unit 315, that is to say, the position of the capsule medical device 303.

Subsequent judgment of whether the capsule medical device 303 has gone outside the control area 17 is the same as in the second embodiment, and therefore, a description thereof is omitted.

With the configuration described above, because the capsule medical device 303 is provided with the wireless transmission unit 315, and because the wireless reception unit 307 and the position calculating unit 333 are provided, the computational unit 35 can judge that the medical device has gone outside the control area.

The capsule medical device 303 is provided with the wireless transmission unit 315, and radio waves are transmitted towards the outside from the wireless transmission unit 315. The wireless reception unit 307 is provided with the plurality of antennas 308 which receive the radio waves transmitted from the wireless transmission unit 315.

Therefore, the wireless reception unit 307 can output a plurality of output signals according to the intensities of the received radio waves. Based on the output signals from the wireless reception unit 307, the position calculating unit 333 can calculate at which position the capsule medical device 303 is located relative to the plurality of antennas 308. The computational unit 35 can judge whether the capsule medical device 303 has gone outside the control area 17 on the basis of the above-mentioned calculation results.

Because the wireless transmission unit 315 and the wireless reception unit 307 are provided, it is possible to perform position measurement of the capsule medical device 303 without using a position-detection-magnetic-field generating coil or the like. For example, when performing image acquisition inside a body cavity of the subject 9 using the capsule medical device 303, it is possible to measure the position etc. of the capsule medical device 303 by using radio waves that transmit image acquisition data. Thus, a position-detection-magnetic-field generating coil or the like that is used only for position measurement is unnecessary, and it is thus possible to simplify the configuration of the capsule-medical-device guidance system 301.

Third Modification of Second Embodiment

A third modification of the second embodiment of the present invention will be described next.

The basic configuration of the capsule-medical-device guidance system of this modification is the same as in the second embodiment and the first embodiment, but a structure associated with position detection of the capsule medical device differs from that in the second embodiment and the first embodiment in that the magnetic-type position calculating unit 133 in the second embodiment and the metal sensors (detection units) 7Y-1 and 7Y-2 in the first embodiment are both provided. In position detection with the metal sensors 7Y-1 and 7Y-2, although it is possible to detect only whether or not the metal portion, that is, the capsule medical device 3, is inside the region defined by the metal sensors 7Y-1 and 7Y-2, the detection range is large. On the other hand, in position detection with the position calculating unit 133, although the detection range is small, it is possible to detect the position and orientation with superior precision compared with the metal sensors 7Y-1 and 7Y-2. Based on detection signals input from the metal sensors 7Y-1 and 7Y-2, the computational unit 35 judges that the capsule medical device 3 has gone outside the control area 17, and also calculates the direction for returning the capsule medical device 3 to the control area 17. The control unit 21 performs control for stopping the guidance magnetic field based on the calculation results from the computational unit 35.

With the configuration described above, an advantage is afforded in that judgment of whether to stop forming the guidance magnetic field based on the capsule medical device 3 going outside the control area 17 is performed using the metal sensors 7Y-1 and 7Y-2 which have rough position calculation precision, whereas the exact position of the capsule medical device 3 can be calculated using the position calculating unit 133 when the capsule medical device 3 is inside the control area. Furthermore, motion control for returning the capsule medical device 3 to the control area 17 etc. may be performed using the calculation results of the position calculating unit 133.

Third Embodiment

Next, a third embodiment of the present invention will be described with reference to FIG. 17.

The basic configuration of the capsule-medical-device guidance system of this embodiment is the same as the second embodiment, but the method of returning the capsule medical device to the control area differs from that in the second embodiment. In this embodiment, therefore, only the vicinity of a structure associated with returning the capsule medical device to the control area will be described, using FIG. 17, and a description of other structures etc. will be omitted.

Figure 17:
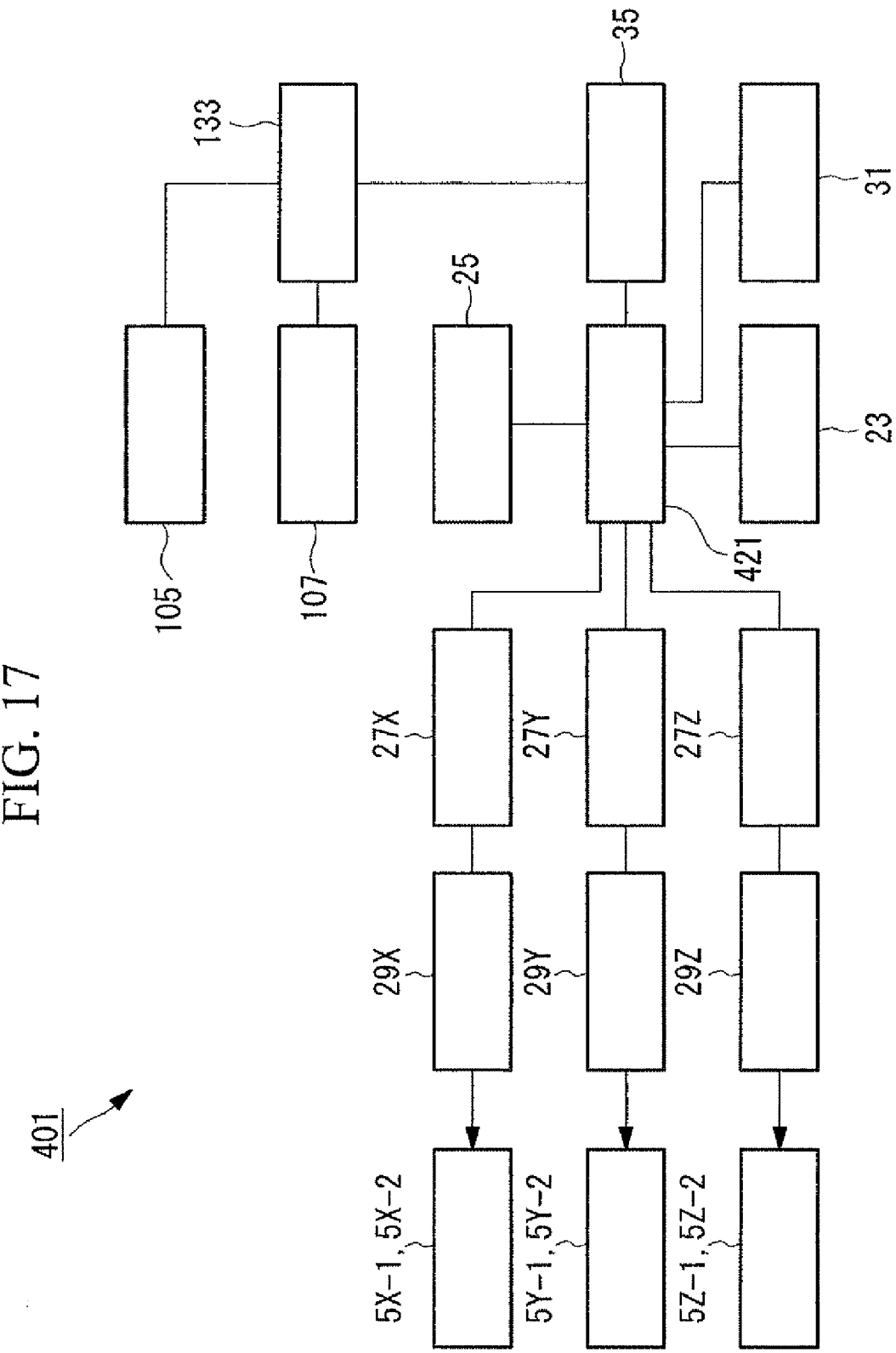
FIG. 17 is a block diagram for explaining the circuit configuration in a capsule-medical-device guidance system according to a third embodiment of the present invention.

FIG. 17 is a block diagram for explaining the circuit configuration in the capsule-medical-device guidance system in this embodiment.

Elements that are identical to those in the second embodiment are assigned the same reference numerals, and a description thereof is omitted.

As shown in FIG. 17, a capsule-medical-device guidance system 401 includes a control unit 421, an operating unit 23, a display unit 25, signal generators 27X, 27Y, and 27Z, guidance-magnetic-field generating coil drivers 29X, 29Y, and 29Z, a driver 31, a computational unit 35, and a position calculating unit 133.

The control unit 421 controls the formation of a guidance magnetic field on the basis of an output from the position calculating unit 133. The computational unit 35 judges that a capsule medical device 103 has gone outside a control area 17 on the basis of an output from the position calculating unit 133. A memory is provided in the computational unit 35; the memory stores the output from a magnetic-field detection unit 107 when only a position-detection magnetic field is applied to the magnetic-field detection unit 107.

Next, the operation of the capsule-medical-device guidance system 401 with the above configuration will be described.

The method of guiding the capsule medical device 103 in this embodiment is roughly the same as that in the first embodiment, and a description thereof is thus omitted.

The method of detecting the position of the capsule medical device 103 in this embodiment is roughly the same as that in the second embodiment, and a description thereof is omitted.

Next, the method of returning the capsule medical device 103 to the control area 17, which is a feature of this embodiment, will be described.

When it is judged by the computational unit 35 that the capsule medical device 103 has gone outside the control area 17, or is about to go outside, the control unit 421 displays an instruction to move the subject 9 on the display unit 25 on the basis of the calculation result of the computational unit 35, and outputs an instruction for returning the capsule medical device 103 to the control area 17. Thereafter, the control unit 421 outputs a signal for stopping generation of the guidance magnetic field.

The instruction for returning the capsule medical device 103 to the control area 17 is, more concretely, an instruction for guiding the capsule medical device 103 in the opposite direction to the one in which it was traveling until that point. For example, an explanation will be given using the case where the capsule medical device 103 travels in the negative direction on the Y-axis and goes outside the control area 17.

When it is judged by the computational unit 35 that the capsule medical device 103 has gone outside the control area 17, the control unit 421 performs control for moving the capsule medical device 103 in the positive direction on the Y-axis. In other words, the control unit 421 outputs to the signal generator 27Z a control signal for reversing the phase (a shift of pi) of the AC signal generated up to that point and outputs to the signal generator 27X a control signal for generating an AC signal identical to the one generated up to that point. By performing such control, the rotation direction of the rotating magnetic field (guidance magnetic field) that guided the capsule medical device 103 in the negative direction on the Y-axis up to that point is reversed. When the rotating direction of the rotating magnetic field is reversed, the capsule medical device 103 is guided in the positive direction on the Y-axis. The control unit 421 guides the capsule medical device 103 by a prescribed amount in the positive direction on the Y-axis and stops generating the guidance magnetic field, as described above. The method of controlling the prescribed amount includes a method of controlling the guidance time of the capsule medical device 103, the number of rotations of the capsule medical device 103 (the rotating magnetic field), and so forth.

As in the first embodiment, an instruction stating "Please move the subject 9 in the positive direction on the Y-axis" is displayed on the display unit 25, and an instruction stating "Please perform a maneuver to return the capsule medical device 103 in the opposite direction" is also displayed. The operator can choose either of the two instructions mentioned above.

In the case of "moving the subject 9 in the positive direction on the Y-axis", the same as in the first embodiment, the control unit 421 may automatically move the bed to move the subject 9, or the operator may operate the bed to move the subject 9.

On the other hand, in the case of "moving the capsule medical device 103 in the opposite direction", the operator inputs an instruction for moving the capsule medical device 103 in the positive direction on the Y-axis, and then the usual guidance operation of the capsule medical device 103 is performed. At this time, the capsule medical device 103 has already been moved by a prescribed amount in the positive direction on the Y-axis by the control unit 421. In such a case, motion control of the bed by the control unit 421 is not performed.

With the configuration described above, the control unit 421 can move the capsule medical device 103 by a prescribed amount in a direction for returning it to the control area 17 by controlling the control magnetic field. Because the capsule medical device 103 approaches the control area by a prescribed amount, guidance control of the capsule medical device 103 becomes easier in subsequent handling, and it is possible to easily prevent the medical device from deviating a great distance from the control area. At the same time, because the distance moved is restricted to a prescribed amount, the capsule medical device 103 does not move to a position away from a position outside the control area. Therefore, the operator of the capsule medical device 103 can easily find the position of the capsule medical device 103, and it is possible to easily prevent the medical device from deviating a great distance from the control area 17.

Because the control unit 421 forms a control magnetic field based on the output from the computational unit 35, it is possible to automatically return the capsule medical device 103 inside the control area 17.

Because the control unit 421 stops forming the control magnetic field after the capsule medical device 103 is made to move in a direction for returning it to the control area 17, it is possible to easily prevent the medical device from deviating a great distance from the control area.

The above-described method of returning the capsule medical device 103 to the control area 17 can also be adapted to other examples or modifications, affording the same advantages as described above.

Figure 18:
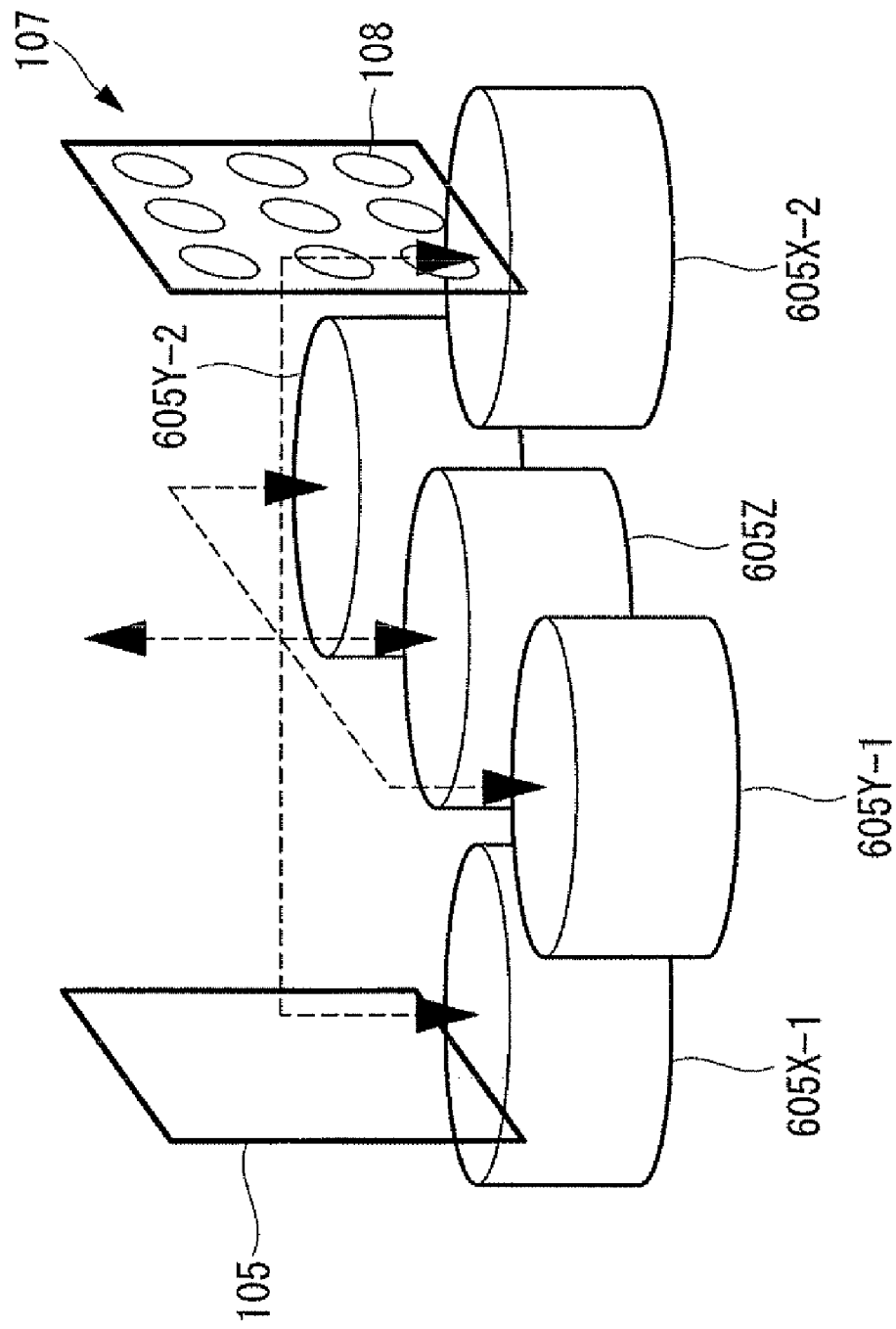
FIG. 18 is a schematic diagram for explaining another embodiment of the capsule-medical-device guidance system in FIG. 11.

FIG. 18 is a schematic diagram for explaining another embodiment of the capsule-medical-device guidance system in FIG. 11.

In the first to third embodiments described above, the coil unit 5 may be formed of the pair of guidance-magnetic-field generating coils 5X-1 and 5X-2, the pair of guidance-magnetic-field generating coils 5Y-1 and 5Y-2, and the pair of guidance-magnetic-field generating coils 5Z-1 and 5Z-2, in a Helmholtz arrangement. However, it is not particularly limited so long as a region with a uniform magnetic field strength distribution is formed; as shown in FIG. 11, it may be formed of guidance-magnetic-field generating coils 605X-1 and 605X-2, guidance-magnetic-field generating coils 605Y-1 and 605Y-2, and a guidance-magnetic-field generating coil 605Z in a planar arrangement.

In the coil arrangement shown in FIG. 18, although a region with a uniform magnetic field intensity distribution is formed in a prescribed area above the guidance-magnetic-field generating coil 605Z, that uniform region is narrower than in the coil arrangements used in the first to third embodiments.

The technical scope of the present invention is not limited to the embodiments described above. Various modifications are possible so long as they do not depart from the spirit of the present invention.

For example, although the control area is a region where the magnetic field strength is substantially uniform, the technical scope of the present invention is not limited thereto. The control area may be enlarged so as to contain part of a region with a strong magnetic field strength gradient (the regions surrounded by the ovals in FIG. 4); or only part of a region with substantially uniform magnetic field strength may be used as the control area. By changing the width of the control area, it is possible to widen the region where the capsule medical device can be freely controlled in exchange for controllability when the capsule medical device returns to the control area in cases where it has moved outside the control area. Alternatively, in exchange for being able to freely control the capsule medical device, it is possible to improve the controllability when the capsule medical device returns to the control area in cases where it has moved outside the control area.

In addition, although propulsion is achieved by converting the rotational motion applied to the capsule medical device by the substantially uniform rotating magnetic field into a propulsive force, the technical scope of the present invention is not limited thereto. It is also possible to apply a magnetic field having a gradient to the capsule medical device so that the capsule medical device is propelled by a magnetic attraction force. The control area in this case is not limited to a substantially uniform area; the control area can be arbitrarily set according to the controllability when the capsule medical device returns to the control area in cases where it has moved outside the control area.

In the embodiments described above, although a description has been given where the present invention is applied to a capsule medical device, the present invention is not limited to a capsule medical device. It can be applied to various other devices, such as catheters and so forth.

The invention claimed is:

1. A medical-device guidance system comprising:
   a medical device with a magnet;
   a guiding unit that forms a control magnetic field for guidance control of the medical device, inside a prescribed control area;
   a detection unit that detects positional information of the medical device;
   a computational unit that judges that the medical device has gone outside the control area on the basis of an output from the detection unit and that calculates a direction for returning the medical device to the control area; and
   a control unit that controls the guiding unit on the basis of an output from the computational unit,
   wherein the control unit stops formation of the control magnetic field when the medical device goes outside the control area.

2. A medical-device guidance system according to claim 1, wherein the medical device is configured to be introduced into a body cavity of a subject, and
   a driver is provided that moves the subject on the basis of an output from the control unit.

3. A medical-device guidance system according to claim 1, wherein on the basis of the output from the computational unit, the control unit forms the control magnetic field for moving the medical device by a prescribed amount in the direction for returning the medical device to the control area and thereafter stops forming the control magnetic field.

4. A medical-device guidance system according to claim 1, wherein the medical device includes a detected portion to be detected by the detection unit, and
the detection unit is disposed in the vicinity of a boundary region of the control area.

5. A medical-device guidance system according to claim 1, wherein:
the medical device includes a magnetic induction coil; and
the detection unit includes a position-detection-magnetic-field forming unit that forms a position-detection magnetic field for inducing an induced magnetic field in the magnetic induction coil,
a magnetic-field detection unit that detects the induced magnetic field generated by the magnetic induction coil, and
a position calculating unit that calculates positional information of the medical device on the basis of an output from the magnetic-field detection unit.

6. A medical-device guidance system according to claim 1, wherein:
the medical device includes a magnetic-field generator that generates a magnetic field; and
the detection unit includes
a magnetic-field detection unit that detects the magnetic field generated by the magnetic-field generator, and
a position calculating unit that calculates positional information of the medical device on the basis of an output from the magnetic-field detection unit.

7. A medical-device guidance system according to claim 1, wherein:
the medical device includes a wireless transmission unit that transmits radio waves; and
the detection unit includes
a plurality of wireless reception units that receive the radio waves, and
a position calculating unit that calculates positional information of the medical device on the basis of output signals from the plurality of wireless reception units.

8. A medical-device guidance system according to claim 1, wherein:
the medical device includes a metal portion; and
the detection unit includes a metal detection unit that is responsive to the metal portion and a position calculating unit that calculates positional information of the medical device on the basis of an output from the metal detection unit.

9. A medical-device guidance system according to claim 1, wherein:
the medical device includes an ultrasonic-wave reflecting portion; and
the detection unit includes an ultrasonic-wave detection unit that detects ultrasonic waves reflected at the ultrasonic-wave reflecting portion, and a position calculating unit that calculates positional information of the medical device on the basis of an output from the ultrasonic-wave detection unit.

10. A medical-device guidance system control method for guidance control, by a control magnetic field formed in a control area, of a medical device in which a magnetic field can be induced and which is disposed inside the control area, the medical-device guidance system control method comprising:
a detecting step of detecting positional information of the medical device;
a calculating step of judging that the medical device has gone outside the control area and calculating a direction for returning the medical device to the control area;
an instructing step of outputting an instruction for moving the medical device in a direction for returning the medical device to the control area; and
a stopping step of stopping formation of the control magnetic field when the medical device goes outside the control area.

11. A medical-device guidance system control method according to claim 10, further comprising:
between the instructing step and the stopping step,
a moving step of relatively moving the medical device and the control area by a prescribed amount in a direction for returning the medical device to the control area.

12. A medical-device guidance system, comprising:
a medical device provided with a magnet;
a guiding unit that forms a control magnetic field for guidance control of the medical device, inside a prescribed control area;
a detection unit that detects positional information and/or directional information of the medical device inside the control area;
a second detection unit that detects positional information of the medical device inside the control area and outside the control area;
a computational unit that judges that the medical device has gone outside the control area on the basis of an output from the second detection unit; and
a control unit that controls the guiding unit on the basis of an output from the computational unit,
wherein the control unit stops formation of the control magnetic field when the medical device goes outside the control area.

13. A medical-device guidance system according to claim 12, wherein the computational unit further calculates a direction for returning the medical device to the control area.

14. A medical-device guidance system according to claim 13, wherein the operating state of the detection unit is controlled on the basis of the output from the second detection unit.

15. A medical-device guidance system according to claim 12, wherein the control unit determines the control magnetic field generated by the guiding unit on the basis of the positional information and/or the directional information detected by the detection unit.

16. A medical-device guidance system according to claim 12, wherein the detection precision of the positional information from the detection unit is better than the detection precision of the positional information from the second detection unit.

17. A medical-device guidance system according to claim 16, wherein the detection unit is formed of a magnetic sensor, and the second detection unit is formed of a metal sensor.

18. A medical-device guidance system according to claim 17, wherein the magnetic sensor and the metal sensor detect the positional information on the basis of magnetic fields of different frequencies.

* * * * *

UNITED STATES PATENT AND TRADEMARK OFFICE
CERTIFICATE OF CORRECTION

PATENT NO.       : 8,386,020 B2
APPLICATION NO.  : 12/307490
DATED            : February 26, 2013
INVENTOR(S)      : Kimura et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1090 days.

Signed and Sealed this

First Day of September, 2015

Michelle K. Lee
*Director of the United States Patent and Trademark Office*